(12) United States Patent
Murakami et al.

(10) Patent No.: US 9,804,139 B2
(45) Date of Patent: Oct. 31, 2017

(54) SENSOR ELEMENT AND GAS SENSOR

(71) Applicant: NGK Insulators, Ltd., Nagoya (JP)

(72) Inventors: Mika Murakami, Nagoya (JP);
Sumiko Horisaka, Kyoto (JP); Hiroki Fujita, Kasugai (JP)

(73) Assignee: NGK Insulators, Ltd., Nagoya (JP)

( * ) Notice: Subject to any disclaimer, the term of this patent is extended or adjusted under 35 U.S.C. 154(b) by 99 days.

(21) Appl. No.: 14/732,949

(22) Filed: Jun. 8, 2015

(65) Prior Publication Data
US 2015/0355142 A1    Dec. 10, 2015

(30) Foreign Application Priority Data

Jun. 9, 2014 (JP) ................. 2014-118808

(51) Int. Cl.
*G01N 33/00* (2006.01)
*G01N 27/407* (2006.01)
*G01N 27/419* (2006.01)

(52) U.S. Cl.
CPC ..... *G01N 33/0039* (2013.01); *G01N 27/4071* (2013.01); *G01N 27/4077* (2013.01); *G01N 27/419* (2013.01)

(58) Field of Classification Search
CPC .... G01N 27/41; G01N 27/62; G01N 27/4071; G01N 27/4077; G01N 27/407;
(Continued)

(56) References Cited

U.S. PATENT DOCUMENTS

2002/0102347 A1* 8/2002 Clyde ................. C23C 4/18
427/58
2004/0112765 A1* 6/2004 Alkemade ........... G01N 27/419
205/784
(Continued)

FOREIGN PATENT DOCUMENTS

JP    02/065113 A1    8/2002
JP    2006-284223 A   10/2006
(Continued)

OTHER PUBLICATIONS

Wakazono JP 2010025793 A Machine Translation.*
(Continued)

*Primary Examiner* — Keith Hendricks
*Assistant Examiner* — Joshua Allen
(74) *Attorney, Agent, or Firm* — Burr & Brown, PLLC

(57) ABSTRACT

A sensor element 101 of a gas sensor 100 includes a blocking portion 65 including an outer blocking layer 67 that is formed to cover, in an upper surface of a multilayer body, at least a part of an upper closest region 6a where an outer pump electrode 23 is not disposed and a distance up to a third inner cavity 61 is minimal. The outer blocking layer 67 does not have conductivity for one or more among various types of substances containing oxygen. The outer blocking layer 67 is disposed between a lead line 93 for the outer pump electrode and the upper surface of the multilayer body to provide insulation therebetween, and is disposed between an upper connector pad 91 and the upper surface of the multilayer body to provide insulation therebetween. A porous protective layer 24 covers the outer pump electrode 23.

16 Claims, 9 Drawing Sheets

(58) Field of Classification Search
CPC .......... G01N 27/404; G01N 27/406–27/4067; G01N 1/2252; G01N 33/0039; G01M 15/10; G01M 15/102; G01M 15/104
See application file for complete search history.

(56) References Cited

U.S. PATENT DOCUMENTS

| | | | |
|---|---|---|---|
| 2011/0147214 A1 | 6/2011 | Fujita et al. | |
| 2011/0220496 A1* | 9/2011 | Oya | G01N 27/407 204/424 |
| 2013/0019655 A1* | 1/2013 | Nakagawa | G01N 27/419 73/31.05 |

FOREIGN PATENT DOCUMENTS

| | | | | |
|---|---|---|---|---|
| JP | EP 2105730 A2 * | 9/2009 | ......... | G01N 27/4071 |
| JP | 2010-025793 A1 | 2/2010 | | |
| JP | 2010-038806 A1 | 2/2010 | | |
| JP | 2010025793 A * | 2/2010 | | |
| JP | 2010038806 A * | 2/2010 | | |
| JP | 2011-102797 A | 5/2011 | | |
| JP | 2011214853 A * | 10/2011 | | |

OTHER PUBLICATIONS

Watanabe JP 2011214853 A Machine Translation.*
Sugaya JP 2010038806 A Machine Translation.*
Extended European Search Report (Application No. 15171215.5) dated Oct. 26, 2015.

* cited by examiner (a)

(b)

SENSOR ELEMENT AND GAS SENSOR

BACKGROUND OF THE INVENTION

1. Field of the Invention

The present invention relates to a sensor element and a gas sensor.

2. Description of the Related Art

There is so far known a gas sensor for detecting the concentration of a specific gas, e.g., NOx, in measurement object gas to be measured, such as automobile exhaust gas. For example, Patent Literatures (PTL) 1 and 2 disclose a gas sensor of the type including a sensor element that has an elongate plate-like shape, and that is formed by stacking a plurality of gas-tight solid electrolyte layers each having oxygen ion conductivity.

FIG. 14 is a schematic sectional view illustrating, in a simplified fashion, one example of a structure of a gas sensor 300 of the above-mentioned related art. As illustrated in the drawing, the gas sensor 300 includes a sensor element 307. The sensor element 307 is an element of a multilayer structure in which dense solid electrolyte layers 301 to 306 each having oxygen ion conductivity are stacked. In the sensor element 307, a measurement-object gas flowing portion through which measurement object gas is introduced is formed between a lower surface of the solid electrolyte layer 306 and an upper surface of the solid electrolyte layer 304. The measurement-object gas flowing portion includes a gas introducing region 310, and first to third inner cavities 320, 340 and 361. An inner pump electrode 322 is formed in the first inner cavity 320, an auxiliary pump electrode 351 is formed in the second inner cavity 340, and a measurement electrode 344 is formed in the third inner cavity 361. Furthermore, an outer pump electrode 323 is formed on an upper surface of the solid electrolyte layer 306. In the gas sensor 300, when the measurement object gas is introduced to the first inner cavity 320 in the measurement-object gas flowing portion, oxygen is pumped out or pumped in between the first inner cavity 320 and the outside of the sensor element 307 in accordance with a control voltage Vp0 that is applied between the outer pump electrode 323 and the inner pump electrode 322. Subsequently, when the measurement object gas is introduced to the second inner cavity 340, oxygen is pumped out or pumped in between the second inner cavity 340 and the outside of the sensor element 307 in accordance with a control voltage Vp1 that is applied between the outer pump electrode 323 and the auxiliary pump electrode 351. After the oxygen concentration of the measurement object gas has been controlled as described above during passage of the measurement object gas through the first inner cavity 320 and the second inner cavity 340, the measurement object gas is introduced to the third inner cavity 361. The concentration of a specific gas in the measurement object gas is then detected on the basis of a current Ip2 that flows when oxygen is pumped out or pumped in through the outer pump electrode 323 and the measurement electrode 344.

CITATION LIST

Patent Literature

[PTL 1] Japanese Unexamined Patent Application Publication No. 2006-284223

[PTL 2] Japanese Unexamined Patent Application Publication No. 2011-102797

SUMMARY OF THE INVENTION

In the related-art gas sensor described above, however, drift of oxygen ions may occur even in a portion of outer surfaces of a multilayer body (sensor element) constituted by the solid electrolyte layers where any electrode is not formed and the solid electrolyte is exposed. In the gas sensor 300 of FIG. 14, for example, oxygen ions may penetrate through the solid electrolyte layer 306 between an atmosphere (measurement object gas) present around a region in the upper surface of the solid electrolyte layer 306, the region being positioned just above the third inner cavity 361, and the third inner cavity 361 without passing through the electrodes. Such a drift of oxygen ions without passing through the electrodes is more likely to occur at a higher temperature or at a larger difference in oxygen concentration between the inside and the outside of the sensor element. With the drift of oxygen ions, accuracy in detecting the concentration of the specific gas in the measurement object gas may lower in some cases. For example, when the drift of oxygen ions without passing through the electrodes occurs in the gas sensor 300 of FIG. 14, noise is generated in the current Ip2 due to the drift of oxygen ions, and the accuracy in detecting the concentration of the specific gas in the measurement object gas lowers in some cases. Because a current utilized to detect the concentration of the specific gas, such as the current Ip2, is a very small current in many cases, it is more susceptible to an influence of the drift of oxygen ions without passing through the electrodes.

The present invention has been made in view of the above-mentioned problem, and a main object of the present invention is to, in a sensor element, suppress oxygen ions from drifting between a measurement electrode mounting space and the outside of a multilayer body without passing through electrodes.

To achieve the above object, the present invention is constituted as follows.

The sensor element of the present invention includes:

a multilayer body formed by stacking a plurality of solid electrolyte layers each having oxygen ion conductivity, and including a measurement-object gas flowing portion that is formed in the multilayer body, and that allows measurement object gas to be introduced from an outside therethrough;

a measurement electrode disposed in a measurement electrode mounting space that is a part of the measurement-object gas flowing portion;

an outer pump electrode disposed on an outer surface of the multilayer body;

a connector electrode for the outer pump electrode, the connector electrode being disposed on the outer surface;

a lead portion for the outer pump electrode, the lead portion being disposed on the outer surface and providing electrical conduction between the outer pump electrode and the connector electrode for the outer pump electrode;

a porous protective layer disposed on the outer surface and covering at least the outer pump electrode; and a blocking portion including an outer blocking layer that is disposed between the lead portion for the outer pump electrode and the outer surface to provide insulation therebetween, that is disposed between the connector electrode for the outer pump electrode and the outer surface to provide insulation therebetween, that is disposed to cover at least a part of a closest region where the outer pump electrode is not disposed and a distance up to the measurement electrode mounting space is minimal among the outer surface, and that does not have conductivity for one or more among various types of substances containing oxygen.

The sensor element includes the blocking portion including the outer blocking layer that is formed to cover, in the outer surface of the multilayer body, at least a part of the closest region where the outer pump electrode is not disposed and the distance up to the measurement electrode mounting space is minimal. Furthermore, the outer blocking layer does not have the conductivity (also called electrical conductivity) for one or more among various types of substances containing oxygen. With those features, the drift of oxygen ions is suppressed in a region in the outer surface of the multilayer body, the region being covered with the blocking portion. In other words, oxygen ions can be suppressed from drifting between the measurement electrode mounting space and the outside of the multilayer body without passing through the electrodes, such as the measurement electrode and the outer pump electrode. In a gas sensor using the above-described sensor element of the present invention, therefore, it is possible, for example, to suppress an influence upon a current between the measurement electrode and the outer pump electrode, the influence being caused by the drift of oxygen ions without passing through the electrodes, and to further improve the accuracy in detecting the concentration of a specific gas in the measurement object gas. As the distance between the measurement electrode mounting space and the outside of the multilayer body decreases, the drift of oxygen ions without passing through the electrodes is more likely to occur between the measurement electrode mounting space and the outside of the multilayer body. In the gas sensor of the present invention, since the outer blocking layer is formed to cover at least a part of the closest region in the outer surface of the multilayer body, the drift of oxygen ions without passing through the electrodes can be suppressed more reliably. Furthermore, in the sensor element of the present invention, the outer blocking layer provides insulation between the lead portion for the outer pump electrode and the outer surface of the multilayer body and insulation between the connector electrode for the outer pump electrode and the outer surface of the multilayer body. Accordingly, the outer blocking layer can serve also as an insulating layer for the lead portion for the outer pump electrode and the connector electrode for the outer pump electrode. Moreover, in the sensor element of the present invention, the outer pump electrode can be protected by the porous protective layer. In this connection, the measurement electrode may be exposed or not exposed to the measurement electrode mounting space. When the measurement electrode is not exposed to the measurement electrode mounting space, the measurement electrode may be covered with a diffusion controlling portion that is made of a porous body.

Here, the "substances containing oxygen" include, for example, not only molecules containing oxygen (O) in chemical formulae, such as $O_2$, CO, $CO_2$, NOx, and $H_2O$, but also ions containing oxygen (O) in chemical formulae. The "ions containing oxygen" include, for example, oxygen ions (also called oxide ions), such as $O^{2-}$ and $O^-$. The blocking portion may be of the nature not having conductivity for one or more among molecules containing oxygen, not having conductivity for one or more among ions containing oxygen, or not having conductivity for one or more among molecules containing oxygen and conductivity for one or more among ions containing oxygen. When a substance, such as a molecule containing oxygen or an ion containing oxygen (except for an oxygen ion), reaches the surface of the solid electrolyte layer, an oxygen ion may be generated from the substance and may drift inside a solid electrolyte. Thus, the above-described effect of suppressing the drift of oxygen ions is obtained when the blocking portion does not have conductivity for substances containing oxygen, without being limited to the case where the blocking portion does not have conductivity for oxygen ions. Preferably, the blocking portion does not have conductivity for one or more among substances, which are present in the measurement object gas and which belong to the substances containing oxygen. As a result, the drift of oxygen ions without passing through the electrodes can be suppressed with higher reliability. Furthermore, the blocking portion preferably has a practically-possible maximum capability of blocking off the measurement object gas (including not only components of the measurement object gas, but also ionized components of the measurement object gas) with respect to the surface of the solid electrolyte. More specifically, the porosity of the blocking portion is preferably 8% or less, and more preferably 5% or less. In addition, the outer blocking layer is preferably formed on a portion of the multilayer body, the portion being exposed to the measurement object gas. In the portion exposed to the measurement object gas, the drift of oxygen ions without passing through the electrodes is more likely to occur. Therefore, forming the outer blocking layer on the exposed portion is very meaningful.

In the sensor element of the present invention, the porous protective layer may cover at least a part of the lead portion for the outer pump electrode and at least a part of the outer blocking layer. With that feature, the porous protective layer can protect not only the outer pump electrode, but also the lead portion for the outer pump electrode and the outer blocking layer.

In the sensor element of the present invention, the outer pump electrode, the connector electrode for the outer pump electrode, and the lead portion for the outer pump electrode may be all disposed on the same surface of the multilayer body. Assuming, for example, that a stacking direction of the multilayer body is defined as an up-and-down direction, the outer pump electrode, the connector electrode for the outer pump electrode, and the lead portion for the outer pump electrode may be all disposed on an upper surface of the multilayer body. Moreover, the outer blocking layer may cover a region in the upper surface of the multilayer body, the region spanning from an end of the outer pump electrode at the side closer to the connector electrode for the outer pump electrode to an end of the upper surface of the multilayer body at the same side as the connector electrode for the outer pump electrode.

The sensor element of the present invention may further include an insulating layer that covers at least a part of the lead portion for the outer pump electrode, the part being not insulated by the outer blocking layer. With that feature, the outer blocking layer provides insulation between the lead portion for the outer pump electrode and the multilayer body, and the insulating layer insulates a part of the lead portion for the outer pump electrode, the part being not insulated by the outer blocking layer. Therefore, the lead portion is insulated with higher reliability. In such a case, the porous protective layer may cover the upper surface of the insulating layer.

In the sensor element of the present invention, the outer blocking layer may cover entirely the closest region. With that feature, the effect of suppressing the drift of oxygen ions without passing through the electrodes is further enhanced with the outer blocking layer.

In the sensor element of the present invention, the outer blocking layer may have a thickness of 1 µm to 30 µm. By setting the thickness of the outer blocking layer to 1 µm or more, the effect of suppressing the drift of oxygen ions without passing through the electrodes is more reliably obtained with the outer blocking layer. By setting the thickness of the outer blocking layer to 30 µm or less, the outer blocking layer can be comparatively easily formed on the solid electrolyte layer.

In the sensor element of the present invention, the multilayer body may be a rectangular parallelepiped, the outer blocking layer may be formed over a plurality of outer surfaces of the multilayer body, and the outer blocking layer may cover all projected regions resulting when perpendicularly projecting the measurement electrode mounting space to the plural outer surfaces for each outer surface over which the outer blocking layer is formed. When the multilayer body is a rectangular parallelepiped and has a plurality of outer surfaces, the projected region resulting when perpendicularly projecting the measurement electrode mounting space to each of the plural outer surfaces is a region in the relevant outer surface where a distance up to the measurement electrode mounting space is minimal. Accordingly, the effect of suppressing the drift of oxygen ions without passing through the electrodes can be further enhanced by, in the case of forming the blocking portion over the plural outer surfaces, forming the outer blocking layer to cover all the projected regions resulting for those outer surfaces over which the outer blocking layer is formed.

In the sensor element of the present invention, the blocking portion may include the outer blocking layer, and an inner blocking layer that is formed to cover at least a part of exposed portions of the solid electrolyte layers in inner peripheral surfaces of the measurement electrode mounting space, and that does not have conductivity for one or more among various types of substances containing oxygen. With that feature, since the blocking portion includes the inner blocking layer in addition to the outer blocking layer, the effect of suppressing the drift of oxygen ions without passing through the electrodes is further enhanced. The types of the substances for which the blocking layer does not have the conductivity may be different or the same between the inner blocking layer and the outer blocking layer.

In the sensor element of the present invention, the sensor element being of the type including the inner blocking layer, the inner blocking layer may have a thickness of 1 µm to 30 µm. By setting the thickness of the inner blocking layer to 1 µm or more, the effect of suppressing the drift of oxygen ions without passing through the electrodes is more reliably obtained with the inner blocking layer. By setting the thickness of the inner blocking layer to 30 µm or less, the inner blocking layer can be comparatively easily formed on the solid electrolyte layer.

In the sensor element of the present invention, the sensor element being of the type including the inner blocking layer, the inner blocking layer may cover at least a part of a region in the inner peripheral surfaces of the measurement electrode mounting space, the region opposing to the closest region. As described above, in a portion where the distance between the measurement electrode mounting space and the outside of the multilayer body is shorter, the drift of oxygen ions without passing through the electrodes is more likely to occur between the measurement electrode mounting space and the outside of the multilayer body. Thus, the drift of oxygen ions without passing through the electrodes can be further suppressed by forming the inner blocking layer that covers at least a part of the above-mentioned region opposing to the closest region. Here, "a region in the inner peripheral surfaces of the measurement electrode mounting space, the region opposing to the closest region" may be, for example, a region at the side opposite to the closest region with the solid electrolyte layer interposed therebetween, or a region resulting when projecting the closest region in the outer surface of the multilayer body to the inner peripheral surface of the measurement electrode mounting space perpendicularly to the closest region. In that case, the inner blocking layer may cover entirely a region in the inner peripheral surfaces of the measurement electrode mounting space, the region opposing to the closest region. With such an arrangement, the effect of suppressing the drift of oxygen ions without passing through the electrodes is further enhanced.

In the sensor element of the present invention, the multilayer body may be a rectangular parallelepiped, and given that the sum of a coverage area a1 where the blocking portion covers projected regions resulting when perpendicularly projecting the measurement electrode mounting space to the plural outer surfaces of the multilayer body for each outer surface, and a coverage area a2 where the blocking portion covers exposed portions of the solid electrolyte layers in the inner peripheral surfaces of the measurement electrode mounting space is denoted by a coverage area A, an area ratio A/B of the coverage area A to an exposed area B of the solid electrolyte layers in the inner peripheral surfaces of the measurement electrode mounting space may be 0.3 or more. With that feature, the effect of suppressing the drift of oxygen ions without passing through the electrodes is further enhanced with the blocking portion. The area ratio A/B is preferably 0.5 or more and more preferably 0.8 or more. The effect of suppressing the drift of oxygen ions without passing through the electrodes is enhanced as the area ratio A/B increases. When the blocking portion does not include the inner blocking layer, a value of the coverage area a2 is 0. Moreover, the exposed area B represents a value involving an area of a region covered with the inner blocking layer. In addition, the coverage area a1 is preferably not less than an area where the measurement electrode covers the solid electrolyte layer. Similarly, the area where the inner blocking layer covers the solid electrolyte layers (i.e., the coverage area a2) is preferably not less than the area where the measurement electrode covers the solid electrolyte layer.

A gas sensor of the present invention includes the sensor element of the present invention according to one of the above-described aspects. Therefore, the gas sensor of the present invention can provide similar advantageous effects to those obtained with the sensor element of the present invention, such as the effect of suppressing an influence upon a current between the measurement electrode and the outer pump electrode, the influence being caused by the drift of oxygen ions without passing through the electrodes, and the effect of further improving the accuracy in detecting the concentration of a specific gas in the measurement object gas.

In the gas sensor of the present invention, a first inner cavity and a second inner cavity may be formed in mentioned order in a region of the measurement-object gas flowing portion from an inlet of the measurement object gas to the measurement electrode mounting space, and the gas sensor may comprise a reference electrode formed inside the multilayer body such that reference gas serving as a reference for detection of concentration of a specific gas in the measurement object gas is introduced to the reference electrode, detection device that detects the concentration of the specific gas in the measurement object gas on the basis of a current flowing when the measurement object gas is introduced to the measurement electrode mounting space and oxygen is pumped out or pumped in through the measurement electrode and the outer pump electrode, a main pump cell that applies, in accordance with an electromotive force generated between an inner main pump electrode, which is formed on the solid electrolyte layer facing the first inner cavity, and the reference electrode, a control voltage between an outer main pump electrode, which is formed on an outer surface of the multilayer body, and the inner main pump electrode, and that pumps out or pumps in oxygen through the inner main pump electrode and the outer main pump electrode such that concentration of oxygen in the first inner cavity becomes a predetermined main pump target concentration, and an auxiliary pump cell that applies, in accordance with an electromotive force generated between an inner auxiliary pump electrode, which is formed on the solid electrolyte layer facing the second inner cavity, and the reference electrode, a control voltage between an outer auxiliary pump electrode, which is formed on an outer surface of the multilayer body, and the inner auxiliary pump electrode, and that pumps out or pumps in oxygen through the inner auxiliary pump electrode and the outer auxiliary pump electrode such that concentration of oxygen in the second inner cavity becomes a predetermined auxiliary pump target concentration. With those features, when the measurement object gas passes through the first inner cavity, the concentration of oxygen in the measurement object gas can be adjusted to the predetermined main pump target concentration. Furthermore, when the measurement object gas passes through the second inner cavity, the concentration of oxygen in the measurement object gas can be adjusted to the predetermined auxiliary pump target concentration. Accordingly, the concentration of oxygen in the measurement object gas reaching the measurement electrode mounting space can be held constant with high accuracy. As a result, the accuracy in detecting the concentration of the specific gas in the measurement object gas can be further improved.

In the gas sensor of the present invention, a first inner cavity may be formed in the measurement-object gas flowing portion over a region spanning from an inlet of the measurement object gas to the measurement electrode mounting space, and the gas sensor may comprise a reference electrode formed inside the multilayer body such that reference gas serving as a reference for detection of concentration of a specific gas in the measurement object gas is introduced to the reference electrode, detection device that detects the concentration of the specific gas in the measurement object gas on the basis of a current flowing when the measurement object gas is introduced to the measurement electrode mounting space and oxygen is pumped out or pumped in through the measurement electrode and the outer pump electrode, and a main pump cell that applies, in accordance with an electromotive force generated between an inner main pump electrode, which is formed on the solid electrolyte layer facing the first inner cavity, and the reference electrode, a control voltage between an outer main pump electrode, which is formed on an outer surface of the multilayer body, and the inner main pump electrode, and that pumps out or pumps in oxygen through the inner main pump electrode and the outer main pump electrode such that concentration of oxygen in the first inner cavity becomes a predetermined main pump target concentration. In that case, the gas sensor of the present invention may further comprise an auxiliary pump cell that applies, in accordance with an electromotive force generated between an inner auxiliary pump electrode, which is formed on the solid electrolyte layer facing the measurement electrode mounting space, and the reference electrode, a control voltage between an outer auxiliary pump electrode, which is formed on an outer surface of the multilayer body, and the inner auxiliary pump electrode, and that pumps out or pumps in oxygen through the inner auxiliary pump electrode and the outer auxiliary pump electrode such that concentration of oxygen in the measurement electrode mounting space becomes a predetermined auxiliary pump target concentration. In that case, the measurement electrode may be covered with a diffusion controlling portion that is made of a porous body.

DETAILED DESCRIPTION OF THE INVENTION

Figure 1:
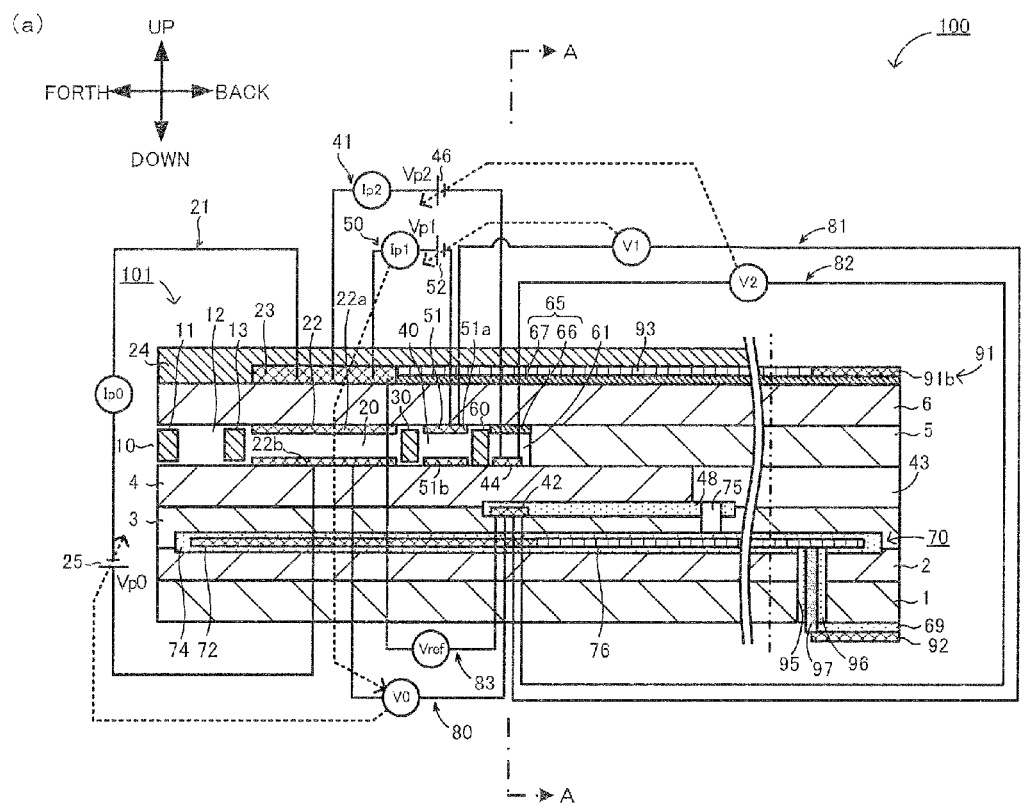
FIG. 1 is a schematic sectional view of a gas sensor 100.
Figure 1:
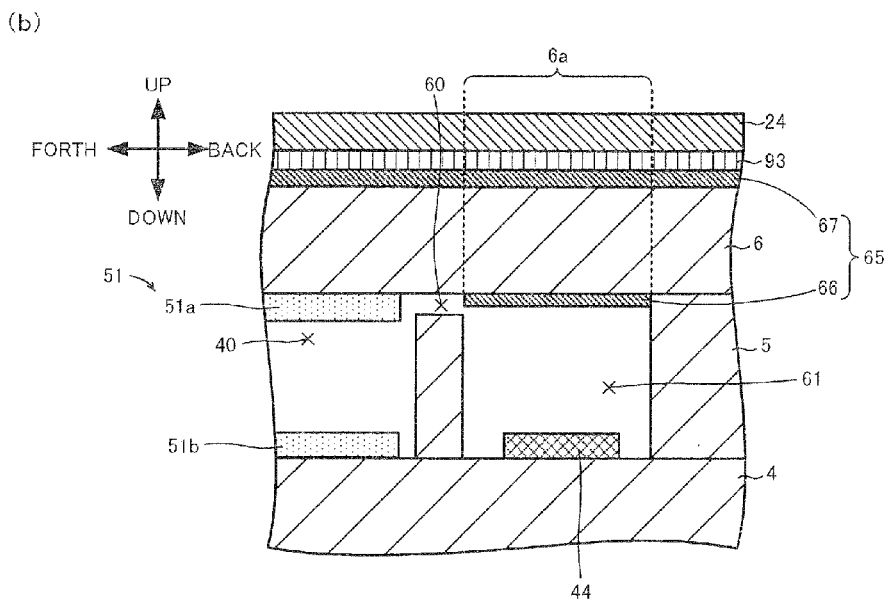
Figure 2:
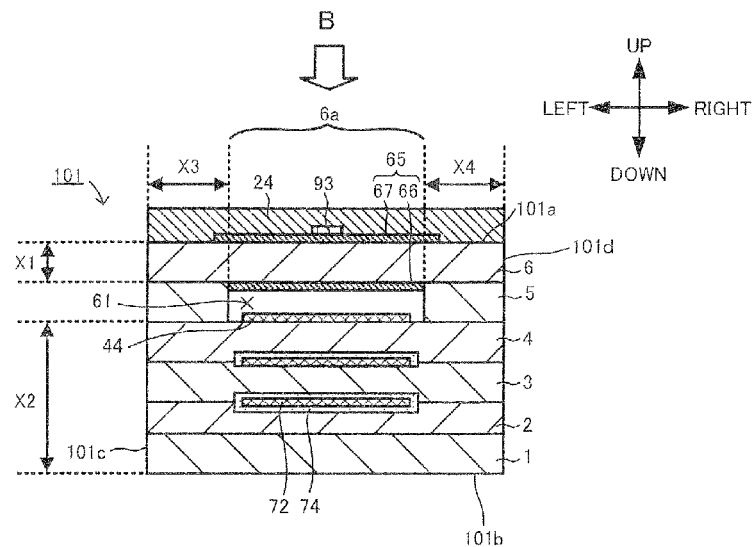
FIG. 2 is a sectional view taken along A-A in FIG. 1(a).
Figure 3:
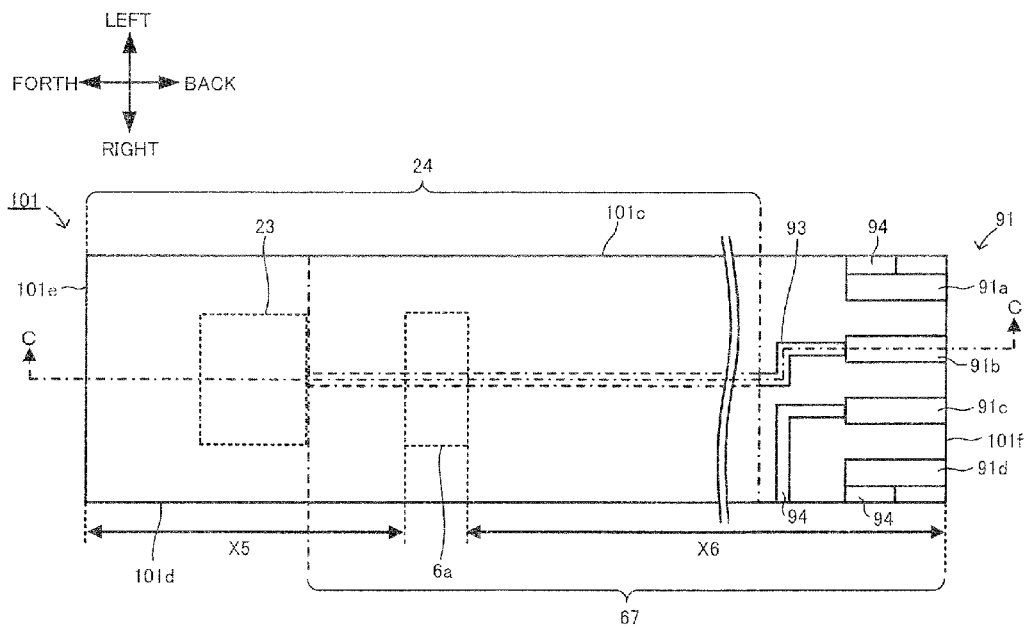
FIG. 3 is a partial view when viewed from a direction denoted by B in FIG. 2.

A basic structure of a gas sensor 100 including a sensor element 101, according to an exemplary embodiment of the present invention, will be described below. FIG. 1 is a schematic sectional view of a gas sensor 100, the view illustrating, in a simplified fashion, one example of a structure of the gas sensor 100. FIG. 1(a) is a schematic sectional view of the gas sensor 100, and FIG. 1(b) is an enlarged view of a region in FIG. 1(a) around a third inner cavity 61. FIG. 2 is a sectional view taken along A-A in FIG. 1(a). FIG. 3 is a partial view when viewed from a direction denoted by B in FIG. 2. The gas sensor 100 includes the sensor element 101 that detects the concentration of a specific gas (NOx in this embodiment) in measurement object gas. The sensor element 101 has an elongate rectangular parallelepiped shape. It is assumed that a lengthwise direction of the sensor element 101 (right and left direction in FIG. 1) is defined as a back and forth direction, and a direction of thickness of the sensor element 101 (up and down direction in FIG. 1) is defined as an up and down direction. Furthermore, a widthwise direction of the sensor element 101 (direction perpendicular to both the back and forth direction and the up and down direction) is defined as a right and left direction (right and left direction in FIG. 2). The section of the sensor element 101, illustrated in FIG. 1(a), corresponds to a sectional view taken along C-C in FIG. 3.

The sensor element 101 is an element including a multi-layer body in which six layers, i.e., a first substrate layer 1, a second substrate layer 2, a third substrate layer 3, a first solid electrolyte layer 4, a spacer layer 5, and a second solid electrolyte layer 6, those layers being each a layer made of a solid electrolyte having oxygen ion conductivity, such as zirconia ($ZrO_2$), are successively stacked in the mentioned order from the lower side when viewed on the drawing. The solid electrolyte forming each of those six layers is a dense and gas-tight substance. The sensor element 101 is manufactured, for example, by carrying out predetermined processing, printing of a circuit pattern, etc. on ceramic green sheets corresponding to the six layers, respectively, stacking those ceramic green sheets, and then firing the stacked sheets into an integral body.

In one end portion (front end portion) of the sensor element 101 and between a lower surface of the second solid electrolyte layer 6 and an upper surface of the first solid electrolyte layer 4, a gas inlet 10, a first diffusion controlling portion 11, a buffer space 12, a second diffusion controlling portion 13, a first inner cavity 20, a third diffusion controlling portion 30, a second inner cavity 40, a fourth diffusion controlling portion 60, and a third inner cavity 61 are successively formed adjacent to each other in the mentioned order in a thoroughly communicating state.

The gas inlet 10, the buffer space 12, the first inner cavity 20, the second inner cavity 40, and the third inner cavity 61 are each an inner space of the sensor element 101, which is formed by boring the spacer layer 5, and which is defined at its top by the lower surface of the second solid electrolyte layer 6, at its bottom by the upper surface of the first solid electrolyte layer 4, and at its sides by lateral surfaces of the spacer layer 5.

The first diffusion controlling portion 11, the second diffusion controlling portion 13, and the third diffusion controlling portion 30 are each provided as two horizontally-elongate slits (each having an opening with a lengthwise direction thereof being a direction perpendicular to the drawing). The fourth diffusion controlling portion 60 is provided as one horizontally-elongate slit (having an opening with a lengthwise direction thereof being the direction perpendicular to the drawing). A region spanning from the gas inlet 10 to the third inner cavity 61 is also called a measurement-object gas flowing portion.

At a location farther away from the one end side of the sensor element 101 than the measurement-object gas flowing portion, a reference gas introducing space 43 is formed at a position between an upper surface of the third substrate layer 3 and a lower surface of the spacer layer 5, and is defined at its sides by lateral surfaces of the first solid electrolyte layer 4. For example, the atmosphere is introduced to the reference gas introducing space 43 as reference gas when the concentration of NOx is measured.

An atmosphere introducing layer 48 is a layer that is made of porous alumina, and that is exposed to the reference gas introducing space 43. The reference gas is introduced to the atmosphere introducing layer 48 through the reference gas introducing space 43. Furthermore, the atmosphere introducing layer 48 is formed in covering relation to a reference electrode 42. The atmosphere introducing layer 48 introduces the reference gas to the reference electrode 42 while giving predetermined diffusion resistance to the reference gas in the reference gas introducing space 43. The atmosphere introducing layer 48 is formed to be exposed to the reference gas introducing space 43 only in a portion of the sensor element 101 at the side closer to the other end (right end) from the reference electrode 42. In comparison with the case where the reference gas introducing space 43 is formed, for example, to extend up to a position just above the reference electrode 42 in FIG. 1, therefore, a path of the reference gas from the reference gas introducing space 43 to the reference electrode 42 is prolonged such that the atmosphere introducing layer 48 can more easily give predetermined high diffusion resistance to the reference gas. Here, as the diffusion resistance given to the reference gas increases, an amount of oxygen contained in the reference gas reaching the reference electrode 42 decreases. Accordingly, by giving the predetermined high diffusion resistance when the oxygen concentration (oxygen partial pressure) in the measurement-object gas flowing portion is measured with the reference electrode 42, it is possible to more easily detect a slight change of the oxygen concentration in the measurement-object gas flowing portion, and to improve detection accuracy. Furthermore, if the reference gas introducing space 43 is formed, for example, to extend up to a position just above the reference electrode 42 in FIG. 1, the reference electrode 42 is more susceptible to poisoning due to the presence of the reference gas. In contrast, this embodiment can prevent such poisoning of the reference electrode 42. It is to be noted that, though the above-mentioned advantageous effects cannot be obtained, the reference electrode 42 may be formed at a position just under the reference gas introducing space 43 in FIG. 1.

The reference electrode 42 is an electrode that is formed in a state sandwiched between the upper surface of the third substrate layer 3 and the first solid electrolyte layer 4. As described above, the atmosphere introducing layer 48 communicating with the reference gas introducing space 43 is disposed around the reference electrode 42. The reference electrode 42 is formed directly on the upper surface of the third substrate layer 3 and is covered with the atmosphere introducing layer 48 at its surfaces except for the surface in contact with the upper surface of the third substrate layer 3. As described later, the oxygen concentration (oxygen partial pressure) in each of the first inner cavity 20, the second inner cavity 40, and the third inner cavity 61 can be measured with the reference electrode 42.

In the measurement-object gas flowing portion, the gas inlet 10 provides a region opened to an external space, and the measurement object gas is taken into the sensor element 101 from the external space through the gas inlet 10. The first diffusion controlling portion 11 serves as a region for giving predetermined diffusion resistance to the measurement object gas that has been taken in through the gas inlet 10. The buffer space 12 is a space provided to introduce the measurement object gas, which has been introduced from the first diffusion controlling portion 11, to the second diffusion controlling portion 13. The second diffusion controlling portion 13 serves as a region for giving predetermined diffusion resistance to the measurement object gas that is introduced from the buffer space 12 to the first inner cavity 20. When the measurement object gas is introduced from the outside of the sensor element 101 to the first inner cavity 20, the measurement object gas is abruptly taken into the inside of the sensor element 101 through the gas inlet 10 depending upon pressure fluctuations of the measurement object gas in the outside space (i.e., upon pulsation of exhaust pressure when the measurement object gas is exhaust gas of an automobile). At that time, the taken-in measurement object gas is not directly introduced to the first inner cavity 20, but it is introduced to the first inner cavity 20 after fluctuations in the concentration of the measurement object gas have been settled through the first diffusion controlling portion 11, the buffer space 12, and the second diffusion controlling portion 13. As a result, the fluctuations in the concentration of the measurement object gas introduced to the first inner cavity 20 are reduced to a substantially negligible level. The first inner cavity 20 is provided as a space for adjusting the partial pressure of oxygen in the measurement object gas that has been introduced through the second diffusion controlling portion 13. The oxygen partial pressure is adjusted with operation of a main pump cell 21.

The main pump cell 21 is an electrochemical pump cell constituted by an inner pump electrode 22 having a ceiling electrode portion 22a that is disposed substantially over an entire region in the lower surface of the second solid electrolyte layer 6, the region facing the first inner cavity 20, an outer pump electrode 23 disposed in a state exposed to the outside space over a region in an upper surface of the second solid electrolyte layer 6, the region corresponding to the ceiling electrode portion 22a, and the second solid electrolyte layer 6 sandwiched between those two electrodes.

The inner pump electrode 22 is formed to extend over respective portions of the solid electrolyte layers at the upper and lower sides (i.e., the second solid electrolyte layer 6 and the first solid electrolyte layer 4) and over portions of the spacer layer 5, those portions defining upper and lower walls and both sidewalls of the first inner cavity 20. More specifically, the ceiling electrode portion 22a is formed on a region in the lower surface of the second solid electrolyte layer 6, the region providing a ceiling surface of the first inner cavity 20, and a bottom electrode portion 22b is formed directly on a region in the upper surface of the first solid electrolyte layer 4, the region providing a bottom surface of the first inner cavity 20. Furthermore, lateral electrode portions (not illustrated) are formed on regions in sidewall surfaces (inner surfaces) of the spacer layer 5, those regions defining both the right and left sidewalls of the first inner cavity 20, to connect the ceiling electrode portion 22a and the bottom electrode portion 22b. Thus, the inner pump electrode 22 is disposed in the form of a tunnel-like structure in a zone where the lateral electrode portions are disposed.

The inner pump electrode 22 and the outer pump electrode 23 are each formed as a porous cermet electrode (e.g., a cermet electrode made of Pt and $ZrO_2$ and containing 1% of Au). The inner pump electrode 22 contacting the measurement object gas is made of a material having a weakened reducing ability with respect to NOx components in the measurement object gas.

In the main pump cell 21, oxygen in the first inner cavity 20 can be pumped out to the outer space, or oxygen in the outer space can be pumped into the first inner cavity 20 by applying a desired pump voltage Vp0 between the inner pump electrode 22 and the outer pump electrode 23, thus causing a pump current Ip0 to flow in a positive direction or a negative direction between the inner pump electrode 22 and the outer pump electrode 23.

Furthermore, to detect the oxygen concentration (oxygen partial pressure) in an atmosphere inside the first inner cavity 20, an electrochemical sensor cell, i.e., an oxygen partial-pressure detection sensor cell 80 for controlling a main pump, is constituted by the inner pump electrode 22, the second solid electrolyte layer 6, the spacer layer 5, the first solid electrolyte layer 4, and the reference electrode 42.

The oxygen concentration (oxygen partial pressure) in the first inner cavity 20 can be determined by measuring an electromotive force V0 in the oxygen partial-pressure detection sensor cell 80 for controlling the main pump. Moreover, the pump current Ip0 is controlled by feedback control of the pump voltage Vp0 given from a variable power supply 25 such that the electromotive force V0 is held constant. As a result, the oxygen concentration in the first inner cavity 20 can be held at a predetermined constant value.

The third diffusion controlling portion 30 serves as a region for applying predetermined diffusion resistance to the measurement object gas of which oxygen concentration (oxygen partial pressure) has been controlled in the first inner cavity 20 with the operation of the main pump cell 21, and for introducing the relevant measurement object gas to the second inner cavity 40.

The second inner cavity 40 is provided as a space where further adjustment of the oxygen partial pressure is performed by an auxiliary pump cell 50 on the measurement object gas that is introduced to the second inner cavity 40 through the third diffusion controlling portion 30 after the adjustment of the oxygen concentration (oxygen partial pressure) in the first inner cavity 20. As a result, the oxygen concentration in the second inner cavity 40 can be held constant with high accuracy, and the gas sensor 100 described above can measure the concentration of NOx with high accuracy.

The auxiliary pump cell 50 is an auxiliary electrochemical pump cell constituted by an auxiliary pump electrode 51 having a ceiling electrode portion 51a, which is disposed substantially over an entire region in the lower surface of the second solid electrolyte layer 6, the region facing the second inner cavity 40, the outer pump electrode 23 (note that a suitable electrode outside the sensor element 101 can be used without being limited to the outer pump electrode 23), and the second solid electrolyte layer 6.

The auxiliary pump electrode 51 is disposed inside the second inner cavity 40 in the form of a tunnel-like structure, which is similar to that of the above-mentioned inner pump electrode 22 disposed inside the first inner cavity 20. More specifically, the ceiling electrode portion 51a is formed on a region in the second solid electrolyte layer 6, the region providing a ceiling surface of the second inner cavity 40, and a bottom electrode portion 51b is formed directly on a region in the upper surface of the first solid electrolyte layer 4, the region providing a bottom surface of the second inner cavity 40. Furthermore, lateral electrode portions (not illustrated) connecting the ceiling electrode portion 51a and the bottom electrode portion 51b are formed respectively on regions in the right and left wall surfaces of the spacer layer 5, those regions defining sidewalls of the second inner cavity 40. Thus, the auxiliary pump electrode 51 has the tunnel-like structure. Similarly to the inner pump electrode 22, the auxiliary pump electrode 51 is also made of a material having a weakened reducing ability with respect to NOx components in the measurement object gas.

In the auxiliary pump cell 50, oxygen in an atmosphere inside the second inner cavity 40 can be pumped out to the outer space, or oxygen can be pumped into the second inner cavity 40 from the outer space by applying a desired voltage Vp1 between the auxiliary pump electrode 51 and the outer pump electrode 23.

Furthermore, to control the oxygen partial pressure in the atmosphere inside the second inner cavity 40, an electrochemical sensor cell, i.e., an oxygen partial-pressure detection sensor cell 81 for controlling an auxiliary pump, is constituted by the auxiliary pump electrode 51, the reference electrode 42, the second solid electrolyte layer 6, the spacer layer 5, and the first solid electrolyte layer 4.

The auxiliary pump cell 50 performs pumping with the aid of a variable power supply 52 of which voltage is controlled in accordance with an electromotive force V1 that is detected by the oxygen partial-pressure detection sensor cell 81 for controlling the auxiliary pump. As a result, the oxygen partial pressure in the atmosphere inside the second inner cavity 40 can be controlled to a low pressure level at which the measurement of NOx is substantially not affected.

In addition, a pump current Ip1 from the variable power supply 52 is used to control the electromotive force of the oxygen partial-pressure detection sensor cell 80 for controlling the main pump. More specifically, the pump current Ip1 is input as a control signal to the oxygen partial-pressure detection sensor cell 80 for controlling the main pump, in order to control the electromotive force V0 thereof. As a result, a gradient of the oxygen partial pressure in the measurement object gas introduced from the third diffusion controlling portion 30 to the second inner cavity 40 is controlled to be always held constant. When the sensor element is used as a NOx sensor, the oxygen concentration in the second inner cavity 40 is held at a constant value of about 0.001 ppm with operations of the main pump cell 21 and the auxiliary pump cell 50.

The fourth diffusion controlling portion 60 serves as a region for applying predetermined diffusion resistance to the measurement object gas of which oxygen concentration (oxygen partial pressure) has been controlled in the second inner cavity 40 with the operation of the auxiliary pump cell 50, and for introducing the relevant measurement object gas to the third inner cavity 61. The fourth diffusion controlling portion 60 has a role of limiting an amount of NOx flowing into the third inner cavity 61.

The third inner cavity 61 is provided as a space where processing to measure the concentration of nitrogen oxides (NOx) in the measurement object gas is performed on the measurement object gas introduced through the fourth diffusion controlling portion 60 after the oxygen concentration (oxygen partial pressure) has been previously adjusted in the second inner cavity 40. The measurement of the NOx concentration is mainly performed in the third inner cavity 61 with operation of a measurement pump cell 41.

The measurement pump cell 41 measures, inside the third inner cavity 61, the concentration of NOx in the measurement object gas. The measurement pump cell 41 is an electrochemical pump cell that is constituted by a measurement electrode 44 formed directly on a region in the upper surface of the first solid electrolyte layer 4, the region facing the third inner cavity 61, the outer pump electrode 23, the second solid electrolyte layer 6, the spacer layer 5, and the first solid electrolyte layer 4. The measurement electrode 44 is a porous cermet electrode. The measurement electrode 44 also functions as a NOx reducing catalyst for reducing NOx that is present in an atmosphere inside the third inner cavity 61.

In the measurement pump cell 41, oxygen generated through decomposition of the nitrogen oxides in an atmosphere around the measurement electrode 44 can be pumped out, and an amount of the generated oxygen can be detected as a pump current Ip2.

To detect the oxygen partial pressure around the measurement electrode 44, an electrochemical sensor cell, i.e., an oxygen partial-pressure detection sensor cell 82 for controlling a measurement pump, is constituted by the first solid electrolyte layer 4, the third substrate layer 3, the measurement electrode 44, and the reference electrode 42. A variable power supply 46 is controlled in accordance with an electromotive force V2 that is detected by the oxygen partial-pressure detection sensor cell 82 for controlling the measurement pump.

The measurement object gas introduced to the second inner cavity 40 reaches the measurement electrode 44 in the third inner cavity 61 through the fourth diffusion controlling portion 60 under the condition of the oxygen partial pressure being controlled. The nitrogen oxides in the measurement object gas around the measurement electrode 44 are reduced ($2NO \rightarrow N_2 + O_2$), thereby generating oxygen. The generated oxygen is subjected to pumping by the measurement pump cell 41. At that time, a voltage Vp2 of the variable power supply 46 is controlled such that the electromotive force V2 detected by the oxygen partial-pressure detection sensor cell 82 for controlling the measurement pump is held constant. Because the amount of oxygen generated around the measurement electrode 44 is in proportion to the concentration of the nitrogen oxides in the measurement object gas, the concentration of the nitrogen oxides in the measurement object gas is calculated by employing the pump current Ip2 in the measurement pump cell 41.

Moreover, when the measurement electrode 44, the first solid electrolyte layer 4, the third substrate layer 3, and the reference electrode 42 are combined to constitute an electrochemical sensor cell that serves as an oxygen partial pressure detection device, the oxygen partial pressure detection device can detect an electromotive force depending on a difference between an amount of oxygen generated with reduction of NOx components, which are present in the atmosphere around the measurement electrode 44, and an amount of oxygen contained in open air as a reference. Accordingly, the concentration of the NOx components in the measurement object gas can also be determined from the detected electromotive force.

In addition, an electrochemical sensor cell 83 is constituted by the second solid electrolyte layer 6, the spacer layer 5, the first solid electrolyte layer 4, the outer pump electrode 23, and the reference electrode 42. The oxygen partial pressure in the measurement object gas outside the gas sensor can be detected from an electromotive force Vref that is obtained by the sensor cell 83.

In the gas sensor 100 constituted as described above, the measurement object gas having the oxygen partial pressure, which is always held at a low constant value (i.e., a value substantially not affecting the measurement of NOx), is applied to the measurement pump cell 41 with the operations of the main pump cell 21 and the auxiliary pump cell 50. Thus, the concentration of NOx in the measurement object gas can be determined on the basis of the pump current Ip2 that flows upon pumping-out of oxygen by the measurement pump cell 41, the oxygen being generated with reduction of NOx substantially in proportion to the concentration of NOx in the measurement object gas.

In order to increase the oxygen ion conductivity of the solid electrolyte, the sensor element 101 further includes a heater section 70 with a role of temperature adjustment to heat the sensor element 101 and to hold its temperature. The heater section 70 includes a heater 72, a heater insulating layer 74, a pressure release hole 75, and a lead line 76 for the heater.

The heater 72 is an electrical resistor formed in a state sandwiched between the second substrate layer 2 and the third substrate layer 3 from below and above, respectively. The heater 72 is connected to a lower connector pad 92, which is a heater electrode, via the lead line 76 for the heater and an intra-hole conductor 97 filled in a lower through-hole 95 (see FIG. 1(*a*)). The heater 72 generates heat with supply of electric power from the outer side through the lower connector pad 92, thereby heating the solid electrolytes, which constitute the sensor element 101, and holding temperatures thereof. The intra-hole conductor 97 is surrounded by an intra-hole insulating layer 96 that covers an inner peripheral surface of the lower through-hole 95, whereby the intra-hole conductor 97 and the inner peripheral surface of the lower through-hole 95 are isolated from each other.

Moreover, the heater 72 is embedded in a state extending over an entire region from the first inner cavity 20 to the third inner cavity 61 such that the sensor element 101 can be entirely controlled to a temperature at which the solid electrolytes are activated.

The heater insulating layer 74 is an insulating layer made of porous alumina, and it is formed over upper and lower surfaces of the heater 72 by employing an insulator made of alumina, for example. The heater insulating layer 74 is formed with intent to provide electrical insulation between the second substrate layer 2 and the heater 72 and electrical insulation between the third substrate layer 3 and the heater 72.

The pressure release hole 75 is formed in a state penetrating through the third substrate layer 3 and communicating with the reference gas introducing space 43. The pressure release hole 75 is provided with intent to relieve a rise of inner pressure attributable to a temperature rise within the heater insulating layer 74.

The sensor element 101 further includes a blocking portion 65. The blocking portion 65 includes an inner blocking layer 66 formed in the third inner cavity 61, and an outer blocking layer 67 formed on an upper surface of the second solid electrolyte layer 6.

The inner blocking layer 66 and the outer blocking layer 67 serve to suppress oxygen ions from drifting inside the multilayer body (specifically, the second solid electrolyte layer 6) without passing through the outer pump electrode 23, the measurement electrode 44 and so on. The inner blocking layer 66 and the outer blocking layer 67 do not have conductivity for one or more among various types of substances containing oxygen, and they are each made of, e.g., alumina, quartz glass, soda glass, silica, mullite, silicon nitride, or silicon carbide. The "substances containing oxygen" include, for example, not only molecules containing oxygen (O) in chemical formulae, such as $O_2$, CO, $CO_2$, NOx, and $H_2O$, but also ions containing oxygen (O) in chemical formulae. The "ions containing oxygen" include, for example, oxygen ions (also called oxide ions), such as $O^{2-}$ and $O^-$. The inner blocking layer 66 and the outer blocking layer 67 preferably have a porosity as small as possible and a thickness as large as possible for the purpose of enhancing the effect of suppressing the drift of oxygen ions without passing through the electrodes. In more detail, the porosity of the blocking portion 65 is preferably 0% or more and 8% or less, and more preferably 5% or less. The thickness of each of the inner blocking layer 66 and the outer blocking layer 67 is preferably 1 μm to 30 μm. By setting the thickness to 1 μm or more, the effect of suppressing the drift of oxygen ions without passing through the electrodes can be obtained with higher reliability. By setting the thickness to 30 μm or less, the inner blocking layer 66 and the outer blocking layer 67 can be each comparatively easily formed on the solid electrolyte layer. The inner blocking layer 66 and the outer blocking layer 67 may be made of the same material, or made of different materials. Similarly, the porosities, the thicknesses, etc. of the inner blocking layer 66 and the outer blocking layer 67 may be the same or different from each other. The outer blocking layer 67 further has a role of insulating a lead line 93 for the outer pump electrode and an upper connector pad 91, both described later, from the upper surface of the second solid electrolyte layer 6, and it is made of an insulating material.

Positions where the inner blocking layer 66 and the outer blocking layer 67 are to be formed are described in detail below. As illustrated in FIGS. 1 to 3, the outer blocking layer 67 directly covers the upper surface of the second solid electrolyte layer 6 of the multilayer body. More specifically, as illustrated in FIGS. 1 and 3, the outer blocking layer 67 covers entirely a region in the upper surface of the second solid electrolyte layer 6, the region spanning from an end of the outer pump electrode 23 at the side closer to the upper connector pad 91 (namely, from a rear end of the outer pump electrode 23) to an end of the upper surface of the second solid electrolyte layer 6 at the same side as the upper connector pad 91. In this embodiment, the rear end of the upper connector pad 91 is aligned with the rear end of the upper surface of the second solid electrolyte layer 6. Thus, the outer blocking layer 67 covers entirely a region in the upper surface of the second solid electrolyte layer 6, the region spanning from the rear end of the outer pump electrode 23 to the rear end of the second solid electrolyte layer 6. In other words, the outer blocking layer 67 is disposed between the upper surface of the second solid electrolyte layer 6 and each of the lead line 93 for the outer pump electrode, a lead line 94, and the upper connector pad 91, which are described in detail later. With such an arrangement, the outer blocking layer 67 provides insulation between the lead line 93 for the outer pump electrode and the upper surface of the second solid electrolyte layer 6, between the lead line 94 and the upper surface of the second solid electrolyte layer 6, and between the upper connector pad 91 and the upper surface of the second solid electrolyte layer 6. Moreover, the outer blocking layer 67 covers entirely an upper closest region 6a in the upper surface of the second solid electrolyte layer 6 where the outer pump electrode 23 is not disposed and a distance up to the third inner cavity 61 is minimal (see FIGS. 1(*b*), 2 and 3). The outer blocking layer 67 does not cover an upper surface of the outer pump electrode 23.

The inner blocking layer 66 is formed to cover, in inner peripheral surfaces of the third inner cavity 61, at least a part of exposed portions of the solid electrolyte layers (i.e., the first and second solid electrolyte layers 4 and 6 and the spacer layer 5). Furthermore, the inner blocking layer 66 covers almost entirely a region in the inner peripheral surfaces of the third inner cavity 61, the region opposing to the upper closest region 6a (namely, a region in the lower surface of the second solid electrolyte layer 6, which region defines a ceiling surface of the third inner cavity 61). In other words, a projected region of the inner blocking layer 66, resulting when perpendicularly projecting the inner blocking layer 66 to the upper surface of the second solid electrolyte layer 6, is substantially aligned with the upper closest region 6a. Here, as illustrated in FIGS. 2 and 3, because the sensor element 101 is a rectangular parallelepiped, the sensor element 101 has six surfaces as outer surfaces of the solid electrolyte layers thereof, i.e., a first surface 101a (upper surface), a second surface 101b (lower surface), a third surface 101c (left lateral surface), a fourth surface 101d (right lateral surface), a fifth surface 101e (front end surface), and a sixth surface 101f (rear end surface). In this embodiment, assuming that the distances from the third inner cavity 61 to the first to sixth surfaces 101a to 101f are denoted by distances X1 to X6, respectively, the third inner cavity 61 is formed such that the distance X1 from the third inner cavity 61 to the first surface 101a is minimal. Accordingly, when a region in any of outer surfaces of the solid electrolyte layers (i.e., the first to sixth surfaces 101a to 101f) where the distance from the region to the third inner cavity 61 is minimal is defined as a "closest region", the upper closest region 6a (i.e., a region in the first surface 101a where the distance up to the third inner cavity 61 is minimal) is the closest region. The upper closest region 6a can also be defined as a projected region resulting when perpendicularly projecting the third inner cavity 61 to the first surface 101a.

Here, an area where the blocking portion 65 covers projected regions resulting when perpendicularly projecting the third inner cavity 61 to the plural outer surfaces (i.e., the first to sixth surfaces 101a to 101f) of the multilayer body for each outer surface is denoted by a coverage area a1. Furthermore, an area where the blocking portion 65 covers the exposed portions of the solid electrolyte layers in the inner peripheral surfaces of the third inner cavity 61 is denoted by a coverage area a2. On that assumption, the blocking portion 65 is preferably formed such that an area ratio A/B of a coverage area A (=the coverage area a1+the coverage area a2) to an exposed area B of the solid electrolyte layers in the inner peripheral surfaces of the third inner cavity 61 is 0.3 or more. In this embodiment, the outer blocking layer 67 covers entirely the upper closest region 6a (=the projected region of the third inner cavity 61 with respect to the first surface 101a). Therefore, an area of the upper closest region 6a is given as the coverage area a1. Moreover, the inner blocking layer 66 covers substantially entirely a region in the inner peripheral surfaces of the third inner cavity 61, the region opposing to the upper closest region 6a. Accordingly, the coverage area a2 is almost equal to the coverage area a1. The exposed area B represents a value involving an area of a region covered with the inner blocking layer 66. Thus, the exposed area B is an area of a part of the inner peripheral surfaces of the third inner cavity 61 where the solid electrolyte layers are exposed, on condition of ignoring the inner blocking layer 66. In this embodiment, because the inner blocking layer 66 and the measurement electrode 44 are formed in the third inner cavity 61, the exposed area B is given by an area of a part of the inner peripheral surfaces (six surfaces) of the third inner cavity 61, the part being not covered with the measurement electrode 44. As the area ratio A/B increases, the effect of suppressing the drift of oxygen ions without passing through the electrodes is enhanced. The area ratio A/B is more preferably set to 0.5 or more, particularly 0.8 or more. In addition, an area (coverage area a2) where the inner blocking layer 66 covers the solid electrolyte layers is preferably not less than an area where the measurement electrode 44 covers the solid electrolyte layer. Similarly, the coverage area a1 is also preferably not less than the area where the measurement electrode 44 covers the solid electrolyte layer. By setting at least one of the coverage area a1 and the coverage area a2 to be not less than the area where the measurement electrode 44 covers the solid electrolyte layer, it is easier to sufficiently obtain the effect of suppressing the drift of oxygen ions without passing through the electrodes.

Furthermore, the upper connector pad 91 is disposed on the upper surface of the second solid electrolyte layer 6 at the rear end side (see FIGS. 1(a) and 3). The upper connector pad 91 functions as a connector electrode for electrical conduction between the sensor element 101 and the outside. The upper connector pad 91 includes a plurality (four in this embodiment) of upper connector pads 91a to 91d. The upper connector pad 91b is electrically connected to the outer pump electrode 23 through the lead line 93 for the outer pump electrode, the lead line 93 being disposed on the upper surface of the outer blocking layer 67 at the upper surface side of the second solid electrolyte layer 6. Similarly, the upper connector pads 91a, 91c and 91d are electrically connected the electrodes inside the sensor element 101 through the lead lines 94 that are disposed on the upper surface of the outer blocking layer 67. The lead lines 94 are each electrically connected to the corresponding electrode inside the sensor element 101 through a not-illustrated lead line that is disposed on the lateral surface (right or left outer surface) of the sensor element 101, or through a not-illustrated lead line that is disposed inside the sensor element 101. The thickness of each of the upper connector pad 91 and the lead line 93 for the outer pump electrode is, e.g., 5 to 20 μm though not being particularly limited thereto. Though omitted in the drawings, on a lower surface of the sensor element 101, not-illustrated other connector pads are disposed in addition to the lower connector pad 92. Like the upper connector pad 91, those connector pads are also electrically connected to the electrodes inside the sensor element 101 through not-illustrated lead lines.

Through the upper connector pad 91 and the connector pads on the lower surface of the sensor element 101, voltages or currents can be applied to the individual electrodes (i.e., the inner pump electrode 22, the outer pump electrode 23, the reference electrode 42, the measurement electrode 44, and the auxiliary pump electrode 51) of the sensor element 101 from the outside, or the voltage or the current of each of those electrodes can be measured. In fact, not only the above-mentioned application of the voltages by the variable power supply 25, the variable power supply 46, and the variable power supply 52, but also the detection of the pump current Ip1 and the electromotive forces V0, V1 and V2 are also performed through the upper connector pad 91 and the connector pads on the lower surface of the sensor element 101.

A lower insulating layer 69 is disposed between a lower surface of the first substrate layer 1 and the lower connector pad 92. Like the outer blocking layer 67, the lower insulating layer 69 provides insulation between the first substrate layer 1 and the lower connector pad 92. In this embodiment, the lower insulating layer 69 covers entirely a substantially rectangular region in the lower surface of the first substrate layer 1, the region spanning from the position of a front end of the lower connector pad 92 to the rear end of the sensor element 101. The lower insulating layer 69 is made of an insulator, e.g., alumina.

Moreover, a porous protective layer 24 covering at least the outer pump electrode 23 is disposed on an upper surface of the multilayer body constituting the sensor element 101. In this embodiment, the porous protective layer 24 covers entirely a region in an upper surface of the sensor element 101, the region spanning from the front end side to the rear end side of the upper surface of the sensor element 101, except for a part of the rear end side thereof including a portion where the upper connector pad 91 is formed (FIGS. 1(a) and 3). Thus, the porous protective layer 24 covers the entirety of the outer pump electrode 23 and most parts of the outer blocking layer 67 and the lead line 93 for the outer pump electrode. Because the porous protective layer 24 does not cover the upper connector pad 91, the upper connector pad 91 is exposed to the outside. Therefore, the porous protective layer 24 does not impede connection between the upper connector pad 91 and the outside. The porous protective layer 24 has a role of suppressing oil components, etc., which are contained in the measurement object gas, from being attached to the outer pump electrode 23 and so on. The porous protective layer 24 is made of a porous body, such as an alumina porous body, a zirconia porous body, a spinel porous body, a cordierite porous body, a titania porous body, or a magnesia porous body. The porosity of the porous protective layer 24 is, e.g., 10 to 50% though not being limited thereto. The thickness of the porous protective layer 24 is, e.g., 5 to 40 µm. The porous protective layer 24 can be formed, for example, by plasma spraying, screen printing, or dipping. While the porous protective layer 24 is disposed to cover the upper surface of the sensor element 101 in this embodiment, the porous protective layer 24 may further cover one or more of the lower surface, the left lateral surface, the right lateral surface, and the front end surface of the sensor element 101.

One example of a method for manufacturing the above-described sensor element 101 of the gas sensor 100 will be described below. First, six unfired ceramic green sheets are prepared each of which contains, as a ceramic component, a solid electrolyte having oxygen ion conductivity, such as zirconia. Each green sheet has a plurality of sheet holes used for positioning in steps of printing and stacking, a plurality of necessary through-holes, etc., which are formed therein in advance. Furthermore, in the green sheet becoming the spacer layer 5, a space serving as the measurement-object gas flowing portion is formed in advance by punching, for example. Similarly, in the green sheet becoming the first solid electrolyte layer 4, a space serving as the reference gas introducing space 43 is formed in advance. A pattern printing process and a drying process are then performed to form various patterns on the ceramic green sheets corresponding to the first substrate layer 1, the second substrate layer 2, the third substrate layer 3, the first solid electrolyte layer 4, the spacer layer 5, and the second solid electrolyte layer 6, respectively. More specifically, the patterns formed in those processes are, for example, patterns for the above-mentioned electrodes, the lead lines, the atmosphere introducing layer 48, the heater section 70, the blocking portion 65, the lower insulating layer 69, the porous protective layer 24, and so on. The pattern printing is performed by coating a pattern forming paste, which is prepared depending on characteristics required for each of objective patterns to be formed, over the corresponding green sheet by utilizing the known screen printing technique. The drying process is also performed by employing some known drying means. After the end of the pattern printing and the drying, an adhesive paste for bonding the green sheets, which correspond to the individual layers of the sensor element, into a stacked state is printed over each of the green sheets and then dried. The green sheets including the adhesive pastes formed thereon are successively stacked in a predetermined order through positioning with the aid of the sheet holes, and are then subjected to a press-bonding process of press-bonding the stacked green sheets into one multilayer body under application of a predetermined temperature and pressure. The multilayer body thus obtained includes the plurality of sensor elements 101. The multilayer body is cut per unit size of the sensor element 101. Each cut piece of the multilayer body is fired at a predetermined firing temperature, whereby the sensor element 101 is obtained. After obtaining the sensor element 101 as described above, the sensor element 101 is placed into a predetermined housing and is assembled into a body (not illustrated) of the gas sensor 100, whereby the gas sensor 100 is obtained. The porous protective layer 24 may be formed and fired after firing the sensor element 101.

In the gas sensor 100 described above, since the inner blocking layer 66 and the outer blocking layer 67 of the sensor element 101 do not have the conductivity for one or more among various types of substances containing oxygen, drift of oxygen ions is suppressed in regions in the surfaces of the multilayer body, the regions being covered with the inner blocking layer 66 and the outer blocking layer 67. For example, when the outer blocking layer 67 does not have the conductivity for oxygen ions, drift of oxygen ions between the outside and the interior of the multilayer body is suppressed in a region in the surfaces of the multilayer body, the region being covered with the outer blocking layer 67. When the inner blocking layer 66 does not have the conductivity for oxygen ions, drift of oxygen ions between the third inner cavity 61 and the interior of the multilayer body is suppressed in a region in the surfaces of the multilayer body, the region being covered with the inner blocking layer 66. The effect of suppressing the drift of oxygen ions is similarly obtained insofar as the inner blocking layer 66 and/or the outer blocking layer 67 does not have the conductivity for one or more among various types of substances containing oxygen, without being limited to the case not having the conductivity for oxygen ions. The reason is that, when an oxygen-containing substance other than oxygen ions reaches the surface of the multilayer body, oxygen ions may be generated from the relevant substance and, in such a case, drift of the generated oxygen ions can be suppressed. Thus, with the presence of the inner blocking layer 66 and the outer blocking layer 67, oxygen ions are suppressed from drifting between the third inner cavity 61 and the outside of the multilayer body without passing through the electrodes, such as the measurement electrode 44 and the outer pump electrode 23.

Correspondence relation between components in this embodiment and components in the present invention is clarified here. The first substrate layer 1, the second substrate layer 2, the third substrate layer 3, the first solid electrolyte layer 4, the spacer layer 5, and the second solid electrolyte layer 6 in this embodiment correspond to a multilayer body in the present invention. The measurement electrode 44 corresponds to a measurement electrode, and the third inner cavity 61 corresponds to a measurement electrode mounting space. The outer pump electrode 23 corresponds to an outer pump electrode. The upper connector pad 91b corresponds to a connector electrode for the outer pump electrode, and the lead line 93 for the outer pump electrode corresponds to a lead portion for the outer pump electrode. The porous protective layer 24 corresponds to a porous protective layer, the outer blocking layer 67 corresponds to an outer blocking layer, and the blocking portion 65 corresponds to a blocking portion. Furthermore, the inner blocking layer 66 corresponds to an inner blocking layer. The outer pump electrode 23 corresponds to an outer main pump electrode and an outer auxiliary pump electrode. The measurement pump cell 41 corresponds to detection device, and the reference electrode 42 corresponds to a reference electrode. The inner pump electrode 22 corresponds to an inner main pump electrode, and the main pump cell 21 corresponds to a main pump cell. The auxiliary pump electrode 51 corresponds to an inner auxiliary pump electrode, and the auxiliary pump cell 50 corresponds to an auxiliary pump cell. It is to be noted that, in this embodiment, one example of the gas sensor of the present invention is also clarified with the above description of the gas sensor 100 including the sensor element 101.

The sensor element 101 of this embodiment, described in detail above, includes the blocking portion 65 including the outer blocking layer 67 that is formed to cover, in the upper surface of the multilayer body, at least a part of the upper closest region 6a where the outer pump electrode 23 is not disposed and the distance up to the third inner cavity 61 is minimal. Furthermore, the outer blocking layer 67 does not have the conductivity for one or more among various types of substances containing oxygen. With those features, the drift of oxygen ions is suppressed in a region in the upper surface of the multilayer body, the region being covered with the blocking portion 65. In other words, oxygen ions can be suppressed from drifting between the third inner cavity 61 and the outside of the multilayer body without passing through the electrodes, such as the measurement electrode 44 and the outer pump electrode 23. If the drift of oxygen ions without passing through the electrodes occurs, noise would be generated, for example, in the pump current Ip2 due to the drift of oxygen ions. As described above, the gas sensor 100 can detect the concentration of NOx in the measurement object gas on the basis of the pump current Ip2. However, if noise is generated in the pump current Ip2, the pump current Ip2 would take a value not accurately reflecting the concentration of NOx, and the detection accuracy would lower. In the gas sensor 100 of this embodiment, since the drift of oxygen ions without passing through the electrodes is suppressed by the blocking portion 65, it is possible to suppress the influence upon the pump current Ip2, and to further improve the accuracy in detecting the concentration of NOx in the measurement object gas. In a portion where the distance between the third inner cavity 61 and the outside of the multilayer body is shorter, the drift of oxygen ions without passing through the electrodes is more likely to occur between the third inner cavity 61 and the outside of the sensor element 101. In the gas sensor 100 of this embodiment, since the outer blocking layer 67 is formed to cover at least a part of the upper closest region 6a in the upper surface of the multilayer body, the drift of oxygen ions without passing through the electrodes can be suppressed more reliably. Furthermore, the outer blocking layer 67 provides insulation between the lead line 93 for the outer pump electrode and the upper surface of the multilayer body and insulation between the upper connector pad 91 and the upper surface of the multilayer body. Therefore, the outer blocking layer 67 can serve also as an insulating layer for the lead line 93 for the outer pump electrode and the upper connector pad 91. Accordingly, the number of operations required in manufacturing the sensor element 101 can be reduced in comparison with, for example, the case where an insulating layer between the upper surface of the multilayer body and each of the lead line 93 for the outer pump electrode and the upper connector pad 91 is formed separately from the outer blocking layer 67. In addition, the outer pump electrode 23 can be protected by the porous protective layer 24.

Since the porous protective layer 24 covers at least a part of the lead line 93 for the outer pump electrode and at least a part of the outer blocking layer 67, the porous protective layer 24 can protect not only the outer pump electrode 23, but also the lead line 93 for the outer pump electrode and the outer blocking layer 67. Moreover, the outer blocking layer 67 covers at least a region in the upper surface of the multilayer body, the region spanning from the end of the outer pump electrode 23 at the side closer to the upper connector pad 91b to the end of the upper surface of the multilayer body at the same side as the upper connector pad 91b.

Since the outer blocking layer 67 covers the entirety of the upper closest region 6a, the effect of suppressing the drift of oxygen ions without passing through the electrodes can be further enhanced with the outer blocking layer 67.

Furthermore, the thickness of each of the inner blocking layer 66, the outer blocking layer 67, and the inner blocking layer 66 is set to 1 µm to 30 µm. By setting the thickness of the outer blocking layer 67 to 1 µm or more, the effect of suppressing the drift of oxygen ions without passing through the electrodes is more reliably obtained with the outer blocking layer 67. By setting the thickness of the outer blocking layer 67 to 30 µm or less, the outer blocking layer 67 can be comparatively easily formed on the solid electrolyte layer. The above-mentioned advantageous effects can also be obtained with the inner blocking layer 66.

Moreover, in the sensor element 101, the blocking portion 65 includes not only the outer blocking layer 67, but also the inner blocking layer 66 that is formed to cover, in the inner peripheral surfaces of the third inner cavity 61, at least a part of the exposed portions of the solid electrolyte layers, and that does not have the conductivity for one or more among various types of substances containing oxygen. Thus, since the blocking portion 65 includes the inner blocking layer 66 in addition to the outer blocking layer 67, the effect of suppressing the drift of oxygen ions without passing through the electrodes is further enhanced.

The inner blocking layer 66 covers entirely a region in the inner peripheral surfaces of the third inner cavity 61, the region opposing to the closest region (i.e., the upper closest region 6a) in the outer surfaces (i.e., the first to sixth surfaces 101a to 101f) of the solid electrolyte layers where the distance up to the third inner cavity 61 is minimal. As described above, in the portion where the distance between the third inner cavity 61 and the outside of the multilayer body is shorter, the drift of oxygen ions without passing through the electrodes is more likely to occur. Thus, the drift of oxygen ions without passing through the electrodes can be further suppressed by forming the inner blocking layer 66 that covers the region opposing to the closest region 6a.

Since the area ratio A/B is 0.3 or more, the drift of oxygen ions without passing through the electrodes can be further suppressed.

Since the porosity of the blocking portion 65 is set to 5% or less, the drift of oxygen ions without passing through the electrodes can be further suppressed.

Still furthermore, the first inner cavity 20, the second inner cavity 40, and the third inner cavity 61 are formed in the measurement-object gas flowing portion. When the measurement object gas passes through the first inner cavity 20, the main pump cell 21 adjusts the concentration of oxygen in the measurement object gas to a predetermined main pump target concentration, and when the measurement object gas passes through the second inner cavity 40, the auxiliary pump cell 50 adjusts the concentration of oxygen in the measurement object gas to a predetermined auxiliary pump target concentration. Therefore, the concentration of oxygen in the measurement object gas reaching the third inner cavity 61 can be held constant at high accuracy. As a result, the accuracy in detecting the concentration of the specific gas in the measurement object gas can be improved.

It is needless to say that the present invention is in no way limited to the above-described embodiment, and that the present invention can be practiced in various forms insofar as not departing from the technical scope of the present invention.

Figure 4:
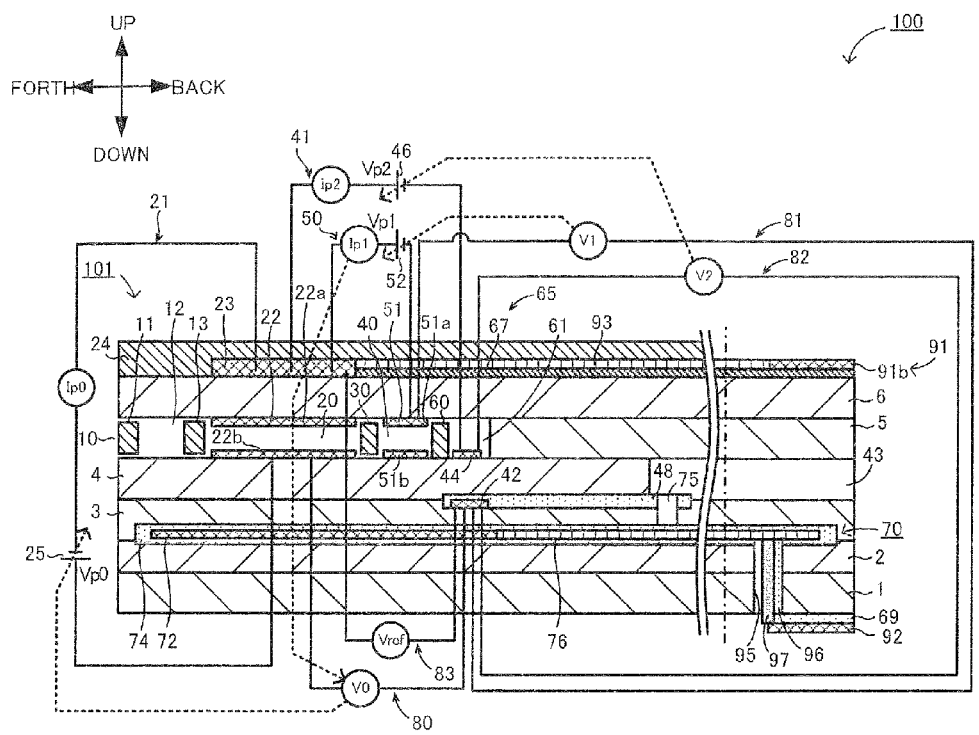
FIG. 4 is a schematic sectional view of a gas sensor 100 according to a modification.

For example, while, in the above-described embodiment, the blocking portion 65 includes both the inner blocking layer 66 and the outer blocking layer 67, the blocking portion 65 is just required to include at least the outer blocking layer 67. Thus, the inner blocking layer 66 may be omitted as illustrated in FIG. 4. Even in such a case, the drift of oxygen ions without passing through the electrodes can be suppressed by the outer blocking layer 67.

Figure 5:
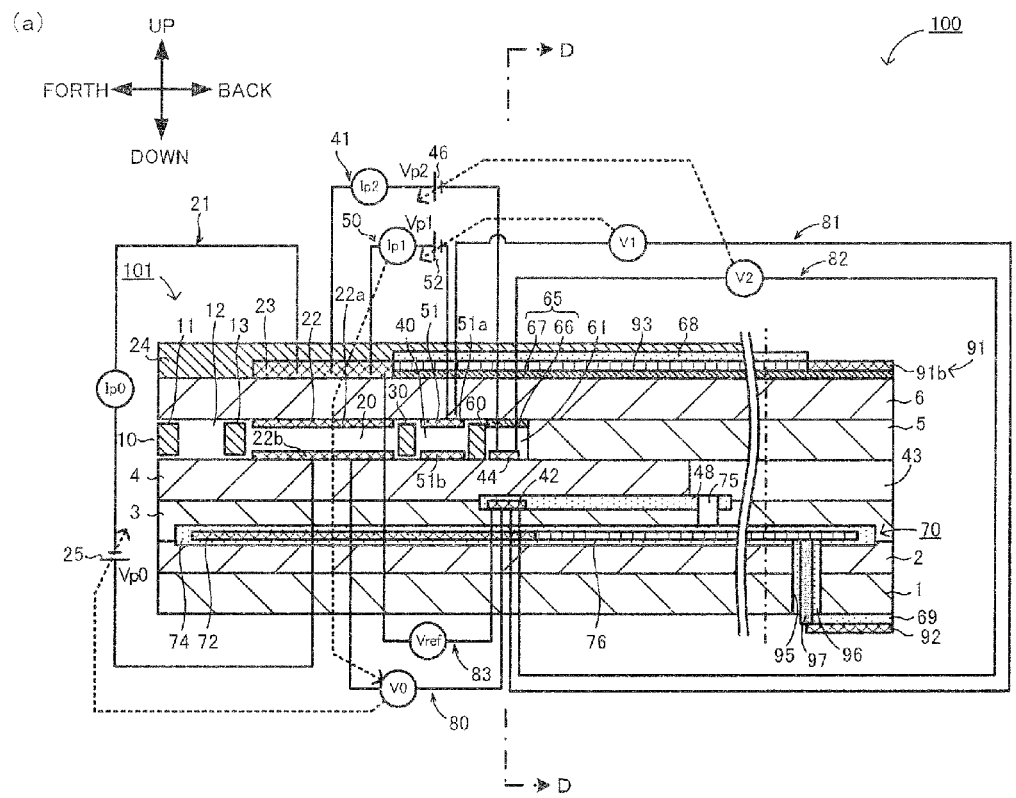
FIG. 5 is a schematic sectional view of a gas sensor 100 according to a modification.
Figure 5:
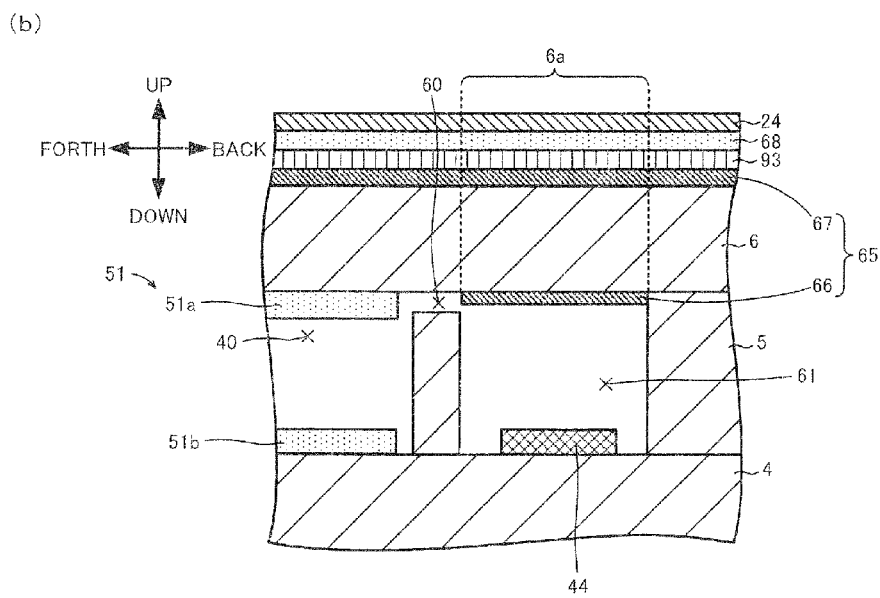
Figure 6:
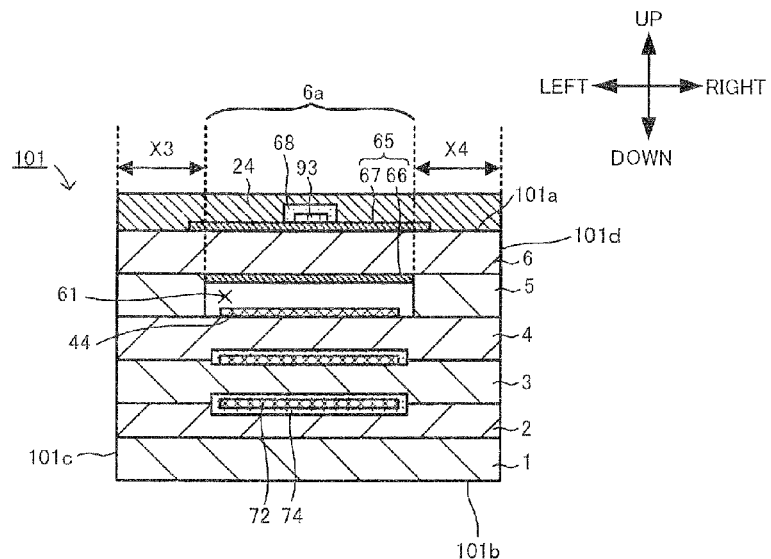
FIG. 6 is a sectional view taken along D-D in FIG. 5.

In the above-described embodiment, the sensor element 101 may include an insulating layer that covers at least a portion of the lead line 93 for the outer pump electrode, the portion being not insulated by the outer blocking layer 67. FIG. 5 is a schematic sectional view of a gas sensor 100 according to a modification including an upper insulating layer 68. FIG. 6 is a sectional view taken along D-D in FIG. 5. In the gas sensor 100 according to this modification, the upper insulating layer 68 covers a region in each of surfaces (lateral and upper surfaces) of the lead line 93 for the outer pump electrode that is formed on the upper surface of the outer blocking layer 67, the region spanning from the side near the outer pump electrode 23 to the side near the upper connector pad 91b. Thus, the upper, lower and lateral surfaces of the lead line 93 for the outer pump electrode are covered with the outer blocking layer 67 and the upper insulating layer 68 each of which is an insulating layer. The upper insulating layer 68 is made of an insulator, e.g., alumina. Suitable one of the above-mentioned materials used for the outer blocking layer 67 may also be used for the upper insulating layer 68. The thickness of the upper insulating layer 68 is 5 μm to 15 μm, for example, though not being limited thereto. The upper insulating layer 68 corresponds to an insulating layer in the present invention. In addition, the upper insulating layer 68 is just required to cover at least a portion of the lead line 93 for the outer pump electrode, the portion being not insulated by the outer blocking layer 67. For example, the upper insulating layer 68 may cover only the upper surface or the lateral surfaces of the lead line 93 for the outer pump electrode.

Figure 7:
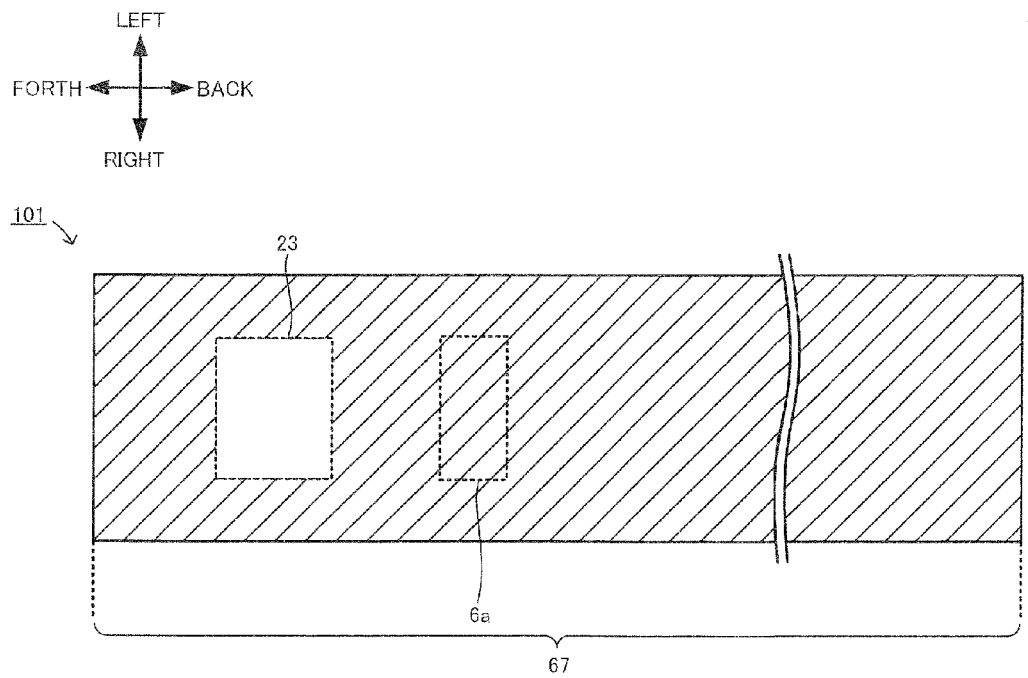
FIG. 7 is a plan view of a sensor element 101 according to a modification.

While, in the above-mentioned embodiment, the outer blocking layer 67 covers entirely a region in the upper surface of the second solid electrolyte layer 6, the region spanning from the rear end of the outer pump electrode 23 to the rear end of the second solid electrolyte layer 6, the present invention is not limited to that embodiment. The outer blocking layer 67 is just required to be disposed between the lead line 93 for the outer pump electrode and the upper surface of the second solid electrolyte layer 6 and between the upper connector pad 91d and the upper surface of the second solid electrolyte layer 6, and to be disposed to cover at least a part of the above-mentioned closest region. For example, the outer blocking layer 67 may cover the second solid electrolyte layer 6 over a larger or smaller area than in the above-described embodiment. As illustrated in FIG. 7, for example, the outer blocking layer 67 may cover entirely the upper surface of the second solid electrolyte layer 6 except for the outer pump electrode 23. By increasing the area where the outer blocking layer 67 covers the upper surface of the second solid electrolyte layer 6, contraction of the outer blocking layer 67 and warping of the sensor element 101 during firing can be further suppressed in comparison with, for example, the case where the outer blocking layer 67 covers just a small part of the upper surface of the second solid electrolyte layer 6. In FIG. 7, the outer blocking layer 67 is denoted by hatching. Moreover, the porous protective layer 24, the upper connector pad 91, the lead line 93 for the outer pump electrode, and the lead lines 94 are omitted in FIG. 7. As an alternative, the outer blocking layer 67 may include a plurality of layers formed in spaced relation, such as represented by the case where one portion of the outer blocking layer 67 covering the upper closest region 6a and the other portion covering the upper connector pad 91 are spaced from each other.

While, in the above-described embodiment, the inner blocking layer 66 covers entirely a region in the inner peripheral surfaces of the third inner cavity 61, the region opposing to the closest region, the inner blocking layer 66 may cover at least a part of the region opposing to the closest region. Alternatively, the inner blocking layer 66 may additionally cover some other region in the inner peripheral surfaces of the third inner cavity 61 than the region opposing to the closest region, or may cover only some other region in the inner peripheral surfaces of the third inner cavity 61 than the region opposing to the closest region. From the viewpoint of enhancing the effect of suppressing the drift of oxygen ions without passing through the electrodes, however, the inner blocking layer 66 preferably covers at least a part of the region opposing to the closest region. The inner blocking layer 66 is not required to cover a region in the inner peripheral surfaces of the third inner cavity 61 where the solid electrolyte layer is not exposed. For example, when the region in the inner peripheral surfaces of the third inner cavity 61 opposing to the closest region partly includes a zone where the solid electrolyte layer is not exposed, the inner blocking layer 66 may cover a part or the entirety of the region opposing to the closest region except for such a zone. In particular, it is preferable to not cover a zone where the electrode, e.g., the measurement electrode 44, is formed.

While, in the above-described embodiment, the outer blocking layer 67 does not cover the outer pump electrode 23, it may cover a part of the outer pump electrode 23. However, because the drift of oxygen ions is suppressed in the part of the outer pump electrode 23, which is covered with the outer blocking layer 67, it is preferable that the outer blocking layer 67 does not cover the outer pump electrode 23.

Figure 8:
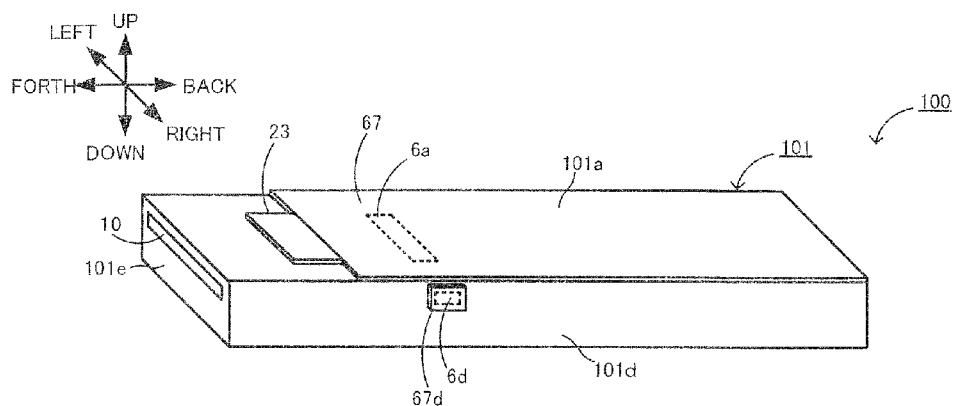
FIG. 8 is a perspective view of a sensor element 101 according to a modification.

While, in the above-described embodiment, the outer blocking layer 67 covers the upper surface of the multilayer body, it may further cover some other outer surface of the multilayer body in addition to the upper surface thereof. FIG. 8 is a perspective view of a gas sensor 100 according to a modification. The porous protective layer 24, the upper connector pad 91, the lead line 93 for the outer pump electrode, and the lead lines 94 are omitted in FIG. 8. In FIG. 8, an outer blocking layer 67d covering a part of the fourth surface 101d is further disposed in addition to the above-mentioned outer blocking layer 67. As an area where the outer blocking layer 67 covers the exposed portions of the solid electrolyte layers increases like this embodiment, the effect of suppressing the drift of oxygen ions without passing through the electrodes is enhanced. As illustrated in the drawing, the outer blocking layer 67d is formed to cover entirely not only a projected region 6d resulting when perpendicularly projecting the third inner cavity 61 to the fourth surface 101d, but also the surroundings of the projected region 6d. When the outer blocking layer is additionally formed on some other outer surface than the surface (e.g., the first surface 101a) that contains the closest region (e.g., the upper closest region 6a), the outer blocking layer is preferably formed to cover all projected regions (e.g., the upper closest region 6a and the projected region 6d in FIG. 8) resulting when perpendicularly projecting the third inner cavity 61 to individual outer surfaces (e.g., the first surface 101a and the fourth surface 101d in FIG. 8) in each of which the outer blocking layer is formed. With such an arrangement, in each of the individual outer surfaces in which the outer blocking layers are formed, it is possible to cover a region (projected region) in the outer surface where the distance up to the third inner cavity 61 is minimal, and to further enhance the effect of suppressing the drift of oxygen ions without passing through the electrodes. It is to be noted that, in FIG. 8, the sum of the area of the upper closest region 6a and the area of the projected region 6d is given as the above-mentioned coverage area a1 because the outer blocking layer covers entirely the upper closest region 6a and the projected region 6d.

While, in the above-described embodiment, the distance X1 is minimal among the distances X1 to X6 illustrated in FIGS. 2 and 3, the present invention is not limited to that embodiment. For example, the distance X4 may be minimal. In such a case, the projected region 6d in FIG. 8 is, by way of example, the closest region. Accordingly, the outer blocking layer is not necessarily required to cover the upper closest region 6a, and it is required instead to be formed in a state covering at least a part of the projected region 6d. Furthermore, it is desired that the inner blocking layer preferentially covers a region in the inner peripheral surfaces of the third inner cavity 61, the region opposing to the projected region 6d, instead of a region in the inner peripheral surfaces of the third inner cavity 61, the region opposing to the upper closest region 6a. As another example, when the distances X3 and X4 among the distances X1 and X6 are equal and minimal, a projected region resulting when perpendicularly projecting the third inner cavity 61 to the third surface 101c, and the projected region 6d are each the closest region. In such a case, the outer blocking layer is not necessarily required to cover the upper closest region 6a, and it is required instead to be formed in a state covering at least a part of one of both the above-mentioned projected regions. Similarly, the inner blocking layer is preferably formed in a state covering at least a part of a region in the inner peripheral surfaces of the third inner cavity 61, the region opposing to at least one of both the above-mentioned projected regions. It is to be noted that the term "closest region" and "upper closest region" do not include a region in the outer surfaces of the multilayer body where the electrode is formed. For example, when the region mentioned as the upper closest region 6a in the above embodiment is covered with the outer pump electrode 23, the upper closest region is given by a region in the upper surface of the second solid electrolyte layer 6 where the distance up to the third inner cavity 61 is minimal, except for a region covered with the outer pump electrode 23. Thus, in such an example, the upper closest region is given by a region in the upper surface of the second solid electrolyte layer 6 around the outer pump electrode 23 where the distance up to the third inner cavity 61 is minimal. Similarly, the term "closest region" and "upper closest region" do not include a portion where the solid electrolyte layer is not present on a surface of the relevant portion, like the gas inlet 10.

While, in the above-described embodiment, the outer blocking layer 67 is disposed on the upper surface of the multilayer body, the surface on which the outer blocking layer 67 is disposed is not limited to the upper surface. For example, when the outer pump electrode 23, the lead line 93 for the outer pump electrode, and the upper connector pad 91 are disposed on some other surface than the upper surface of the multilayer body, the outer blocking layer 67 is also required to be disposed on the same surface as the surface on which the lead line 93 for the outer pump electrode and the upper connector pad 91 are disposed, to thereby provide insulation between the outer surface of the multilayer body and each of the lead line 93 for the outer pump electrode and the upper connector pad 91.

While, in the above-described embodiment, the main pump cell 21 is constituted by the outer pump electrode 23, the inner pump electrode 22, and the second solid electrolyte layer 6, another electrode (called an outer main pump electrode) disposed outside the sensor element 101 may be used instead of the outer pump electrode 23. Likewise, while, in the above-described embodiment, the auxiliary pump cell 50 is constituted by the auxiliary pump electrode 51, the outer pump electrode 23, and the second solid electrolyte layer 6, another electrode (called an outer auxiliary pump electrode hereinafter) disposed outside the sensor element 101 may be used instead of the outer pump electrode 23. When other pump electrodes than the outer pump electrode 23 are formed on the outer surfaces of the multilayer body as in the above-mentioned case, the outer blocking layer 67 is preferably disposed not to cover those pump electrodes. Moreover, when leads and connector pads electrically conducted to the other pump electrodes than the outer pump electrode 23 are formed on the outer surfaces of the multilayer body, the outer blocking layer 67 is preferably disposed between each of those leads and connector pads and the corresponding outer surface of the multilayer body, thereby providing insulation therebetween.

While, in the above-described embodiment, the inner pump electrode 22 is formed as a tunnel-like electrode constituted by the ceiling electrode portion 22a, the bottom electrode portion 22b, and the lateral electrode portions, the inner pump electrode 22 is not limited to the tunnel-like form. For example, the inner pump electrode 22 may be formed by only the ceiling electrode portion 22a, or only the bottom electrode portion 22b. Similarly, the auxiliary pump electrode 51 is also not limited to the tunnel-like form.

Figure 9:
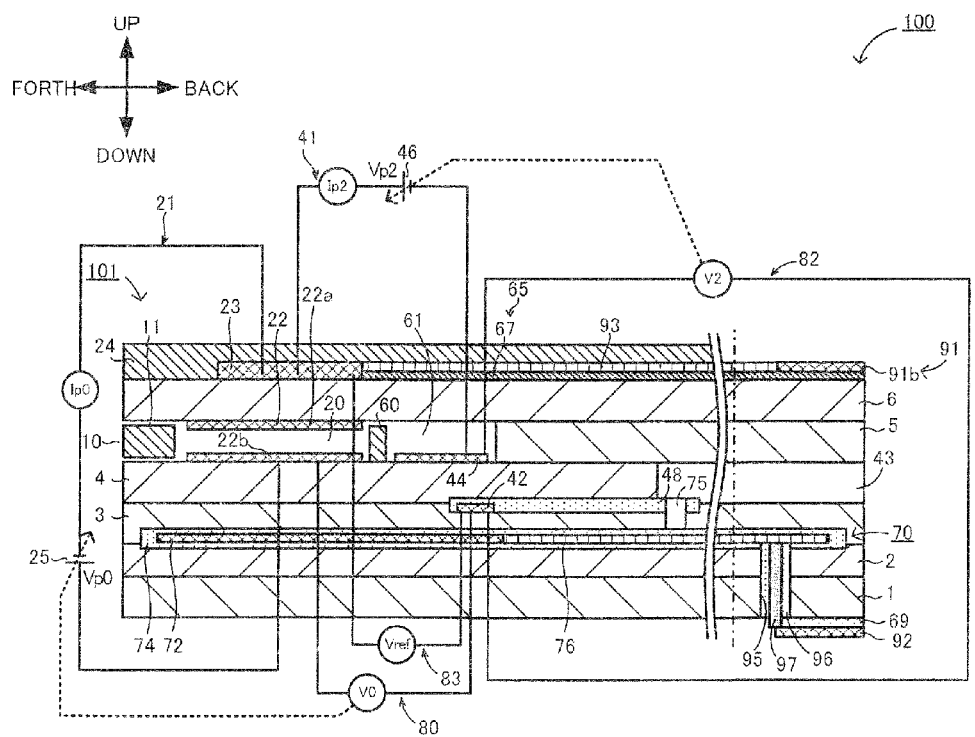
FIG. 9 is a schematic sectional view of a gas sensor 100 according to a modification.

While, in the above-described embodiment, the sensor element 101 of the gas sensor 100 includes the first inner cavity 20, the second inner cavity 40, and the third inner cavity 61, the present invention is not limited to that embodiment. For example, the sensor element 101 may have a structure not including the second inner cavity 40. FIG. 9 is a schematic sectional view of a gas sensor 100 according to a modification representing the above-mentioned case. In the gas sensor 100 illustrated in FIG. 9, the blocking portion 65 does not include the inner blocking layer 66. As illustrated in FIG. 9, in the gas sensor 100 according to this modification, the gas inlet 10, the first diffusion controlling portion 11, the first inner cavity 20, the fourth diffusion controlling portion 60, and the third inner cavity 61 are successively formed adjacent to each other in the mentioned order in a thoroughly communicating state between the lower surface of the second solid electrolyte layer 6 and the upper surface of the first solid electrolyte layer 4. Furthermore, unlike the above-described embodiment, the gas sensor 100 does not include the auxiliary pump cell 50 and the oxygen partial-pressure detection sensor cell 81 for controlling the auxiliary pump. In the gas sensor 100 constituted as described above, the measurement object gas having the oxygen partial pressure, which is always held at a low constant value (i.e., a value substantially not affecting the measurement of NOx), is applied to the measurement pump cell 41 with the operation of the main pump cell 21. Thus, the concentration of NOx in the measurement object gas can be determined on the basis of the pump current Ip2 that flows upon pumping-out of oxygen by the measurement pump cell 41, the oxygen being generated with reduction of NOx substantially in proportion to the concentration of NOx in the measurement object gas. The gas sensor constituted as described above can also suppress the drift of oxygen ions without passing through the electrodes, can reduce the influence upon the pump current Ip2, and can further improve the accuracy in detecting the concentration of NOx in the measurement object gas similarly to the gas sensor of the above-described embodiment, by providing the blocking portion 65 including at least the outer blocking layer 67 as in the above-described embodiment. Moreover, since the outer blocking layer 67 provides insulation between the lead line 93 for the outer pump electrode and the upper surface of the multilayer body and insulation between the upper connector pad 91 and the upper surface of the multilayer body, the outer blocking layer 67 can serve also as an insulating layer for the lead line 93 for the outer pump electrode and the upper connector pad 91. In addition, the outer pump electrode 23 can be protected by the porous protective layer 24.

While the above-described embodiment represents an example in which the sensor element of the present invention is practiced as the sensor element 101 including the variable power supplies 25, 46 and 52, etc., the sensor element of the present invention may be practiced in the form including the sensor element 101 alone with omission of the variable power supplies 25, 46 and 52, the external wirings, etc.

While, in the above-described embodiment, the gas inlet 10 is formed at the front end surface of the sensor element 101, the position of the gas inlet 10 is not limited to the front end surface insofar as the measurement object gas can be introduced from the outside therethrough. For example, the gas inlet 10 may be formed in the upper surface of the sensor element 101 (i.e., in the upper surface of the second solid electrolyte layer 6).

While, in the above-described embodiment, the upper connector pads 91a, 91c and 91d are electrically conducted to the electrodes inside the sensor element 101 through the lead lines 94, the present invention is not limited to that embodiment. For example, one or more of the upper connector pads 91a, 91c and 91d may be electrically conducted to the electrodes inside the sensor element 101 through conductors filled in through holes like the lower connector pad 92.

Figure 10:
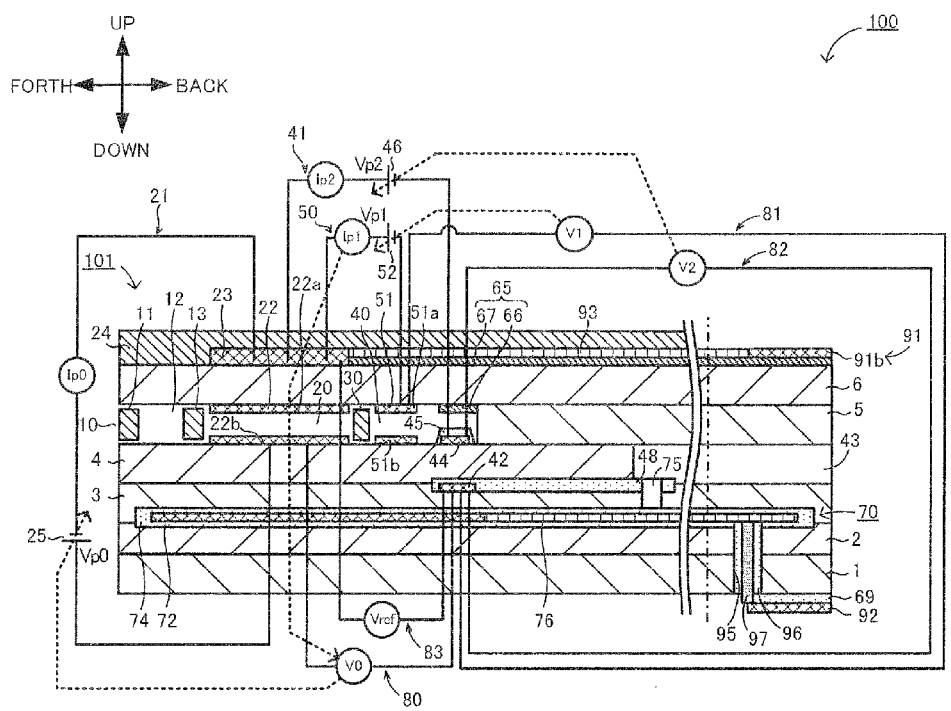
FIG. 10 is a schematic sectional view of a gas sensor 100 according to a modification.

While, in the above-described embodiment, the measurement electrode 44 is disposed in the state exposed to the third inner cavity 61 (measurement electrode mounting space), the present invention is not limited to that embodiment. For example, the measurement electrode may be covered with a diffusion controlling portion that is made of a porous body. FIG. 10 is a schematic sectional view of a gas sensor 100 according to a modification representing such a case. A sensor element 101 of the gas sensor 100 according to this modification does not include the fourth diffusion controlling portion 60 and the third inner cavity 61. Instead, the measurement electrode 44 is disposed in the second inner cavity 40 and is covered with a fourth diffusion controlling portion 45. In the sensor element 101 according to this modification, as illustrated in FIG. 10, the gas inlet 10, the first diffusion controlling portion 11, the buffer space 12, the second diffusion controlling portion 13, the first inner cavity 20, the third diffusion controlling portion 30, and the second inner cavity 40 are successively formed adjacent to each other in the mentioned order in a thoroughly communicating state between the lower surface of the second solid electrolyte layer 6 and the upper surface of the first solid electrolyte layer 4. A portion extending from the gas inlet 10 to the second inner cavity 40 serves as the measurement-object gas flowing portion. The measurement electrode 44 is disposed on the upper surface of the first solid electrolyte layer 4 inside the second inner cavity 40. Thus, the second inner cavity 40 corresponds to the measurement electrode mounting space in the present invention. The measurement electrode 44 is covered with the fourth diffusion controlling portion 45. In other words, the measurement electrode 44 is not exposed to the second inner cavity 40. The fourth diffusion controlling portion 45 is a film made of a ceramic porous body, e.g., alumina ($Al_2O_3$). Like the fourth diffusion controlling portion 60 in the above-described embodiment, the fourth diffusion controlling portion 45 has a role of restricting an amount of NOx flowing into the measurement electrode 44. The fourth diffusion controlling portion 45 further functions as a protective film. The gas sensor 100 constituted as described above can also suppress the drift of oxygen ions without passing through the electrodes, can reduce the influence upon the pump current Ip2, and can further improve the accuracy in detecting the concentration of NOx in the measurement object gas similarly to the gas sensor of the above-described embodiment, by providing the blocking portion 65 including at least the outer blocking layer 67 as in the above-described embodiment. Moreover, since the outer blocking layer 67 provides insulation between the lead line 93 for the outer pump electrode and the upper surface of the multilayer body and insulation between the upper connector pad 91 and the upper surface of the multilayer body, the outer blocking layer 67 can serve also as an insulating layer for the lead line 93 for the outer pump electrode and the upper connector pad 91. In addition, the outer pump electrode 23 can be protected by the porous protective layer 24.

EXAMPLES

The cases of practically fabricating the sensor elements will be described below as Examples. It is to be noted that the present invention is not limited to the following Examples.

Example 1

Ten sensor elements, each having the same structure as that of the sensor element 101 illustrated in FIGS. 1 to 3, were fabricated as Example 1 in accordance with the above-described manufacturing method. Unlike the sensor element illustrated in FIGS. 1 to 3, however, the outer blocking layer 67 was disposed to cover only a part of the upper closest region 6a, the boundary between the lead line 93 for the outer pump electrode and the upper surface of the second solid electrolyte layer 6, the boundary between the upper connector pad 91 (including 91a to 91d) and the upper surface of the second solid electrolyte layer 6, and the boundaries between the lead lines 94 and the upper surface of the second solid electrolyte layer 6. The porous protective layer 24 in Example 1 was made of alumina, and it had the porosity of 35% and the thickness of 20 μm. The lead lines 94 were made of platinum. The inner blocking layer 66 and the outer blocking layer 67 were made of alumina, and they had the porosity of 5% and the thickness of 5 μm. The area where the measurement electrode 44 covered the solid electrolyte layer was set to 0.4 $mm^2$, the exposed area B of the solid electrolyte layers in the inner peripheral surfaces of the third inner cavity 61 was set to 1.4 $mm^2$, the area (coverage area a2) where the inner blocking layer 66 covered the solid electrolyte layer was set to 0.7 $mm^2$, and the area (coverage area a1) where the outer blocking layer 67 covered the closest region 6a was set to 0.4 $mm^d$. As a result, the coverage area A was 1.1 $mm^2$, and the area ratio A/B was 0.8.

Example 2

Ten sensor elements, each being the same as the sensor element of Example 1, were fabricated as Example 2 in a similar manner except for that the blocking portion 65 includes only the outer blocking layer 67 (the area ratio A/B=0.4/1.4=0.3).

Comparative Example 1

Ten sensor elements, each being the same as the sensor element of Example 1 except for the following points, were fabricated as Comparative Example 1. The blocking portion 65 included only the outer blocking layer 67 without including the inner blocking layer 66 (i.e., the coverage area a2=0 mm$^2$). The outer blocking layer 67 was disposed in a state not covering the upper closest region 6a at all (i.e., the coverage area a1=0 mm$^2$), but covering only the boundary between the lead line 93 for the outer pump electrode and the upper surface of the second solid electrolyte layer 6, the boundary between the upper connector pad 91 (including 91a to 91d) and the upper surface of the second solid electrolyte layer 6, and the boundaries between the lead lines 94 and the upper surface of the second solid electrolyte layer 6. The lead line 93 for the outer pump electrode was formed in bypassing relation to the upper closest region 6a such that the arranged position of the lead line 93 for the outer pump electrode did not overlap the upper closest region 6a. The area ratio A/B was 0/1.4=0.

[Evaluation Test 1]

Figure 11:
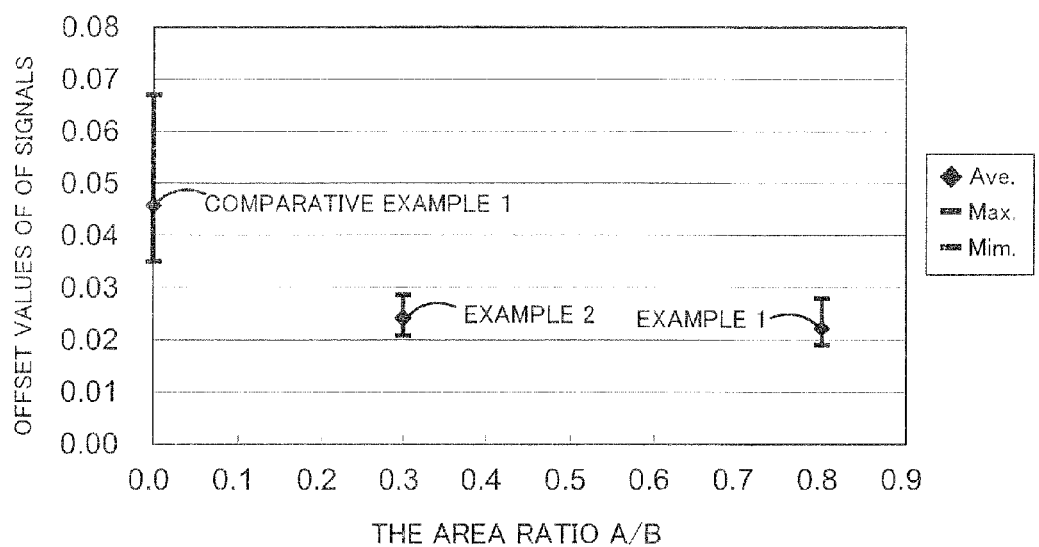
FIG. 11 is a graph representing offset values of NOx signals in Examples 1 and 2 and Comparative Example 1.

The sensor elements of Examples 1 and 2 and Comparative Example 1 were each kept at a temperature (800° C.), i.e., a level obtained during a usual driving mode, by a heater in a predetermined atmosphere (nitrogen concentration=79%, oxygen concentration=18%, NOx concentration=0%, and moisture=3%), and an offset value of a NOx signal (i.e., the pump current Ip2 of the measurement pump cell 41) was measured. The measurement was performed on ten sensor elements for each of Examples 1 and 2 and Comparative Example 1. A maximum value, a minimum value, and an average value of the ten measured current values were determined. The determined results are depicted in FIG. 11. As seen from the drawing, in any of Examples 1 and 2 in which the outer blocking layer 67 covered the upper closest region 6a, the offset value of the NOx signal had a tendency to become lower than that in Comparative Example 1. Comparing Examples 1 and 2, the offset value of the NOx signal had a tendency to become lower in Example 1 including both the inner blocking layer 66 and the outer blocking layer 67. Comparing Examples 1 and 2 and Comparative Example 1 in terms of a value of the area ratio A/B, the offset value of the NOx signal had a tendency to become lower in Examples 1 and 2 each having the value of the area ratio A/B of 0.3 or more than that in Comparative Example 1. In Example 1 having the value of the area ratio A/B of 0.5 or more, the offset value of the NOx signal had a tendency to become even lower. Here, the offset value of the NOx signal in the atmosphere is theoretically 0 µA, and a larger offset value means that the pump current Ip2 flows in a larger amount attributable to factors irrespective of the NOx concentration. It is thought that, in Examples 1 and 2, the offset value of the NOx signal is reduced because the drift of oxygen ions without passing through the electrodes is suppressed with the presence of the outer blocking layer 67 covering the upper closest region 6a.

[Evaluation Test 2]

Figure 12:
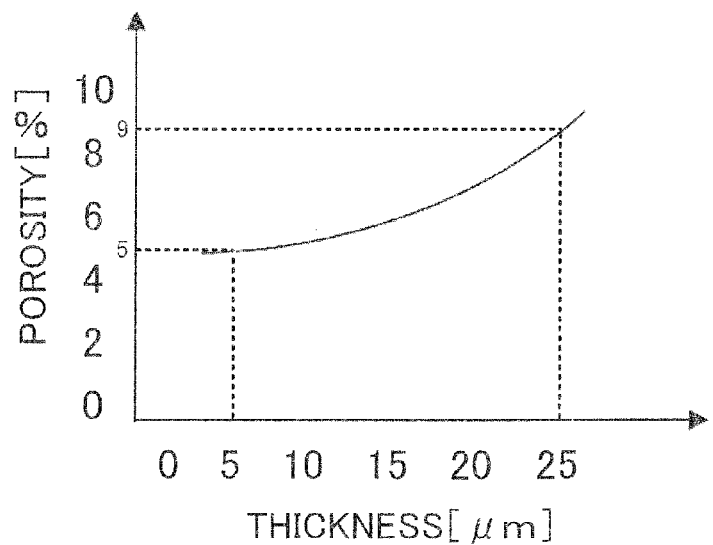
FIG. 12 is a graph representing a boundary line that defines a region where the offset values of the NOx signals are satisfactory, when the thickness and the porosity of a blocking portion 65 are changed variously.

For the sensor elements of Example 2, the offset value of the NOx signal was measured when the thickness and the porosity of the blocking portion 65 (outer blocking layer 67) were changed variously. The measured results are depicted in FIG. 12. A curve of FIG. 12 plots the correspondence between the thickness and the porosity when the offset value of the NOx signal takes 0.03 µA. The plot means that, in a region below the curve, the offset value of the NOx signal is 0.03 µA or less and a satisfactory result is obtained. As seen from the drawing, at a smaller value of the porosity, the satisfactory result was obtained even with the thickness taking a smaller value. For example, when the porosity of the blocking portion 65 was set to 9%, the satisfactory result was obtained with the thickness of 25 µm or more. Furthermore, when the porosity of the blocking portion 65 was set to 5% or less, the satisfactory result was obtained with the thickness being in the range of 5 µm or more.

[Evaluation Test 3]

Figure 13:
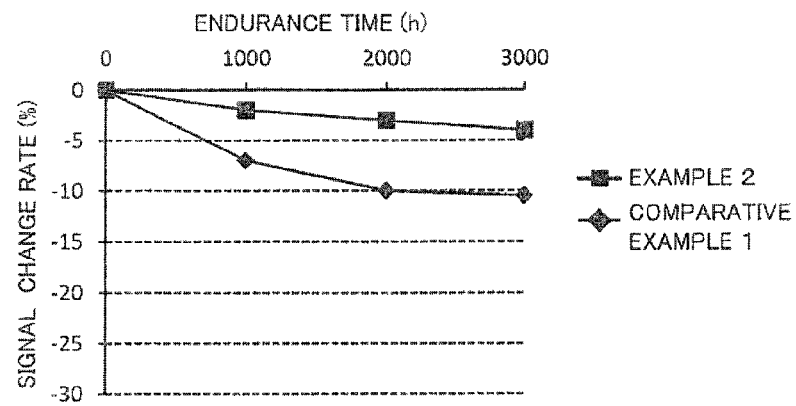
FIG. 13 is a graph representing signal change rates in Example 2 and Comparative Example 1.
Figure 14:
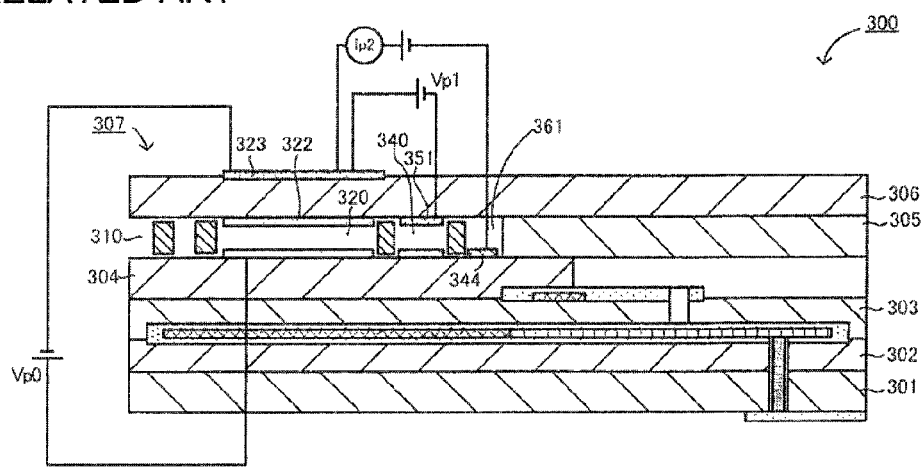
FIG. 14 is a schematic sectional view of a gas sensor 300 of related art.

Durability was evaluated for the sensor elements of Example 2 and Comparative Example 1. In more detail, initially, the sensor element was kept at a temperature (800° C.), i.e., a level obtained during the usual driving mode, by a heater in the atmosphere, and was left to stand in such a state for a predetermined endurance time. Then, a value of a signal (i.e., the pump current Ip2 of the measurement pump cell 41), which was used to measure the NOx concentration in the sensor element after the lapse of the endurance time, was measured in an atmosphere (nitrogen concentration=96.95%, oxygen concentration=0%, NOx concentration=500 ppm, and moisture=3%) in which the NOx concentration was 500 ppm. That signal value was measured after the lapse of each period of endurance time while the endurance time was changed from 0 hour, to 1000 hours, to 2000 hours, and to 3000 hours. The measured results are depicted in FIG. 13. FIG. 13 depicts the relation between a signal change rate from a reference value and the endurance time, the reference value being set as the signal value in each of Example 2 and Comparative Example 1 when the endurance time was 0 hour. When an absolute value of the signal change rate has a larger negative value, this means that reduction of sensitivity in detecting the NOx concentration with the lapse of time is larger (i.e., durability is lower). As seen from FIG. 13, Example 2 showed such a tendency that, even with an increase of the endurance time, the signal change rate was not so reduced and the absolute value of the signal change rate was relatively small (the signal change rate was near 0%) in comparison with Comparative Example 1. It is thought that, in Example 2, a load exerted on the electrodes is reduced and the durability is improved in comparison with Comparative Example 1 because an undesired current, such as noise mixed in the pump current Ip2, is suppressed with the presence of the outer blocking layer 67 covering the upper closest region 6a.

By citation of Japanese Patent Application No. 2014-118808 filed for a patent in Japan on Jun. 9, 2014, the contents of the specification, the drawings, and the claims, disclosed in the relevant Japanese Patent Application are all incorporated in this specification.

What is claimed is:
1. A sensor element comprising:
   a multilayer body formed by stacking a plurality of solid electrolyte layers each having oxygen ion conductivity, and including a measurement-object gas flowing portion that is formed in the multilayer body, and that allows measurement object gas to be introduced from an outside therethrough;
   a measurement electrode disposed in a measurement electrode mounting space that is a part of the measurement-object gas flowing portion;
   an outer pump electrode disposed on an outer surface of the multilayer body;

a connector electrode for the outer pump electrode, the connector electrode being disposed on the outer surface of the multilayer body;

a lead portion for the outer pump electrode, the lead portion being disposed on the outer surface of the multilayer body and providing electrical conduction between the outer pump electrode and the connector electrode for the outer pump electrode;

a porous protective layer disposed on the outer surface of the multilayer body and covering at least the outer pump electrode; and a blocking portion including an outer blocking layer that is disposed between the lead portion for the outer pump electrode and the outer surface of the multilayer body, that is disposed between the connector electrode for the outer pump electrode and the outer surface of the multilayer body, that is disposed to cover at least a part of a closest region where the outer pump electrode is not disposed and a distance up to the measurement electrode mounting space is minimal among the outer surface of the multilayer body, and that does not have conductivity for one or more substances containing oxygen.

2. The sensor element according to claim 1, further comprising an insulating layer that covers at least a part of the lead portion for the outer pump electrode, the part being not insulated by the outer blocking layer.

3. The sensor element according to claim 1, wherein the outer blocking layer covers entirely the closest region.

4. The sensor element according to claim 1, wherein the outer blocking layer has a thickness of 1 µm to 30 µm.

5. The sensor element according to claim 1, wherein the multilayer body is a rectangular parallelepiped,
the outer blocking layer is formed over a plurality of outer surfaces of the multilayer body, and
the outer blocking layer covers all projected regions resulting when perpendicularly projecting the measurement electrode mounting space to the plural outer surfaces for each outer surface over which the outer blocking layer is formed.

6. The sensor element according to claim 1, wherein the blocking portion includes the outer blocking layer, and an inner blocking layer that is formed to cover at least a part of exposed portions of the solid electrolyte layers in inner peripheral surfaces of the measurement electrode mounting space, and that does not have conductivity for one or more among various types of substances containing oxygen.

7. The sensor element according to claim 6, wherein the inner blocking layer has a thickness of 1 µm to 30 µm.

8. The sensor element according to claim 6, wherein the inner blocking layer covers at least a part of a region in the inner peripheral surfaces of the measurement electrode mounting space, the region opposing to the closest region.

9. The sensor element according to claim 6, wherein the inner blocking layer covers entirely a region in the inner peripheral surfaces of the measurement electrode mounting space, the region opposing to the closest region.

10. The sensor element according to claim 1, wherein the multilayer body is a rectangular parallelepiped, and
given that the sum of a coverage area a1 where the blocking portion covers projected regions resulting when perpendicularly projecting the measurement electrode mounting space to the plural outer surfaces of the multilayer body for each outer surface, and a coverage area a2 where the blocking portion covers exposed portions of the solid electrolyte layers in inner peripheral surfaces of the measurement electrode mounting space is denoted by a coverage area A, an area ratio A/B of the coverage area A to an exposed area B of the solid electrolyte layers in the inner peripheral surfaces of the measurement electrode mounting space is 0.3 or more.

11. The sensor element according to claim 10, wherein the area ratio A/B is 0.5 or more.

12. The sensor element according to claim 10, wherein the area ratio A/B is 0.8 or more.

13. The sensor element according to claim 1, wherein the blocking portion has a porosity of 5% or less.

14. A gas sensor including the sensor element according to claim 1.

15. The gas sensor according to claim 14,
wherein a first inner cavity and a second inner cavity are formed in mentioned order in a region of the measurement-object gas flowing portion from an inlet of the measurement object gas to the measurement electrode mounting space, and
the gas sensor comprises:
a reference electrode formed inside the multilayer body such that reference gas serving as a reference for detection of concentration of a specific gas in the measurement object gas is introduced to the reference electrode;
detection device that detects the concentration of the specific gas in the measurement object gas on the basis of a current flowing when the measurement object gas is introduced to the measurement electrode mounting space and oxygen is pumped out or pumped in through the measurement electrode and the outer pump electrode;
a main pump cell that applies, in accordance with an electromotive force generated between an inner main pump electrode, which is formed on the solid electrolyte layer facing the first inner cavity, and the reference electrode, a control voltage between an outer main pump electrode, which is formed on an outer surface of the multilayer body, and the inner main pump electrode, and that pumps out or pumps in oxygen through the inner main pump electrode and the outer main pump electrode such that concentration of oxygen in the first inner cavity becomes a predetermined main pump target concentration; and
an auxiliary pump cell that applies, in accordance with an electromotive force generated between an inner auxiliary pump electrode, which is formed on an solid electrolyte layer facing the second inner cavity, and the reference electrode, a control voltage between an outer auxiliary pump electrode, which is formed on an outer surface of the multilayer body, and the inner auxiliary pump electrode, and that pumps out or pumps in oxygen through the inner auxiliary pump electrode and the outer auxiliary pump electrode such that concentration of oxygen in the second inner cavity becomes a predetermined auxiliary pump target concentration.

16. The gas sensor according to claim 14,
wherein a first inner cavity is formed in a region of the measurement-object gas flowing portion from an inlet of the measurement object gas to the measurement electrode mounting space, and
the gas sensor comprises:
a reference electrode formed inside the multilayer body such that reference gas serving as a reference for detection of concentration of a specific gas in the measurement object gas is introduced to the reference electrode;

detection device that detects the concentration of the specific gas in the measurement object gas on the basis of a current flowing when the measurement object gas is introduced to the measurement electrode mounting space and oxygen is pumped out or pumped in through the measurement electrode and the outer pump electrode; and a main pump cell that applies, in accordance with an electromotive force generated between an inner main pump electrode, which is formed on the solid electrolyte layer facing the first inner cavity, and the reference electrode, a control voltage between an outer main pump electrode, which is formed on an outer surface of the multilayer body, and the inner main pump electrode, and that pumps out or pumps in oxygen through the inner main pump electrode and the outer main pump electrode such that concentration of oxygen in the first inner cavity becomes a predetermined main pump target concentration.

* * * * *